US008470371B2

(12) United States Patent
Uchegbu et al.

(10) Patent No.: US 8,470,371 B2
(45) Date of Patent: Jun. 25, 2013

(54) POLYMERIC MICELLAR CLUSTERS AND THEIR USES IN FORMULATING DRUGS

(75) Inventors: Ijeoma F. Uchegbu, London (GB); Andreas G. Schatzlein, London (GB); Xueliang Hou, Glasgow (GB)

(73) Assignee: University College London, London (GB)

( * ) Notice: Subject to any disclaimer, the term of this patent is extended or adjusted under 35 U.S.C. 154(b) by 721 days.

(21) Appl. No.: 12/376,827

(22) PCT Filed: Aug. 8, 2007

(86) PCT No.: PCT/GB2007/003016
§ 371 (c)(1),
(2), (4) Date: Feb. 26, 2010

(87) PCT Pub. No.: WO2008/017839
PCT Pub. Date: Feb. 14, 2008

(65) Prior Publication Data
US 2010/0159014 A1    Jun. 24, 2010

(30) Foreign Application Priority Data

Aug. 9, 2006   (GB) .................................. 0615834.9

(51) Int. Cl.
| | |
|---|---|
| *A61K 9/14* | (2006.01) |
| *A61K 31/573* | (2006.01) |
| *A61K 31/05* | (2006.01) |
| *A61K 38/13* | (2006.01) |
| *A61K 31/565* | (2006.01) |
| *A61K 31/568* | (2006.01) |

(52) U.S. Cl.
USPC ........... 424/489; 514/181; 514/731; 514/182; 514/178; 514/449; 514/27; 514/31

(58) Field of Classification Search
USPC ....................................................... 424/489
See application file for complete search history.

(56) References Cited

FOREIGN PATENT DOCUMENTS
| | | | | |
|---|---|---|---|---|
| WO | WO-2004/026912 A1 | 4/2004 | | |
| WO | WO2004026912 A1 * | 4/2004 | .................... | 424/489 |
| WO | WO-2008/017839 A1 | 2/2008 | | |

OTHER PUBLICATIONS

Uchegbu, Ijeoma F., et al. "Controls on Polymer Molecular Weight May Be Used to Control the Size of Palmitoyl Glycol Chitosan Polymeric Vesicles." Langmuir, 2001, 17, 631-636. Published on the web, Jan. 5, 2001.*
Wang et al. "Controls on Polymer Molecular Weight May Be Used to Control the Size of Palmitoyl Glycol Chitosan Polymeric Vesicles", Langmuir, 2001, 17, 631-636. Published on Web Jan. 5, 2001. Submitted in IDS of Sep. 29, 2011.*
Kirkpatrick, P. "Pressures in the Pipeline" *Nature Reviews*, May 2003, 2(5): 337.
Wenlock, M.G. et al. "A Comparison of Physiochemical Property Profiles of Development and Marketed Oral Drugs" *Journal of Medicinal Chemistry*, Mar. 27, 2003, 46(7): 1250-1256.
Rowe, R.C. et al., *Handbook of Pharmaceutical Excipients*, Fifth Edition, 2006, London: Pharmaceutical Press.
Cheng, H.Y. et al. "Micellar Aggregation of Poloxamer 213 and Its Interaction with Cholesterol Derivatives" *Journal of Pharmaceutical Sciences*, Oct. 1990, 79(10): 907-912.
Alexandridis, P. et al. "Micellization of Poly(ethylene oxide)-Poly(propylene oxide)-Poly(ethylene oxide) Triblock Copolymers in Aqueous Solutions: Thermodynamics of Copolymer Association" *Macromolecules*, Apr. 1994, 27(9): 2414-2425.
Nam, Y.S. et al. "New micelle-like polymer aggregates made from PEI-PLGA diblock copolymers: micellar characteristics and cellular uptake" *Biomaterials*, May 2003, 24(12): 2053-2059.
Krishna, A.K. et al. "Micellar Solubilization of a New Antimalarial Drug, β-Arteether" *Journal of Pharmaceutical Sciences*, Jul. 1989, 78(7): 574-576.
Strickley, R.G. "Solubilizing Excipients in Oral and Injectable Formulations" *Pharmaceutical Research*, Feb. 2004, 21(2): 201-230.
Trapani, G. et al. "Effect of 2-hydroxypropyl-β-cyclodextrin on the aqueous solubility of the anaesthetic agent propofol (2,6-diisopropylphenol)" *International Journal of Pharmaceutics*, Aug. 9, 1996, 139(1-2): 215-218.
Arnanson, T. et al. "Effects of structural variations of non-ionic surfactants on micellar erucyl and solubilization: surfactants based on erucyl and behenyl ($C_{22}$) alcohols" *Journal of Pharmacy and Pharmacology*, Sep. 1980, 32(1): 381-385.
Ong, J.T.H. et al. "Micellar Solubilization of Timobesone Acetate in Aqueous and Aqueous Propylene Glycol Solutions of Nonionic Surfactants" *Pharmaceutical Research*, Nov. 1988, 5(11): 704-708.
Shuai, X. et al. "Micellar carriers based on block copolymers of poly(ε-caprolactone) and poly(ethylene glycol) for doxorubicin delivery" *Journal of Controlled Release*, Aug. 27, 2004, 98(3): 415-426.
Kwon, G.S. et al. "Block copolymer micelles as long-circulating drug vehicles" *Advanced Drug Delivery Reviews*, Sep. 1995, 16(2-3): 295-309.
Allen, C. et al. "Nano-engineering block copolymer aggregates for drug delivery" *Colloids and Surfaces B: Biointerfaces*, Nov. 1999, 16(1): 3-27.

(Continued)

*Primary Examiner* — Richard Schnizer
*Assistant Examiner* — Audrea Buckley
(74) *Attorney, Agent, or Firm* — Saliwanchik, Lloyd & Eisenschenk

(57) ABSTRACT

Polymeric micellar clusters formed from amphiphilic carbohydrate polymers and their uses in formulating drugs is disclosed, and in particular the finding that amphiphilic carbohydrate polymers are capable of self assembling to form micellar clusters in which the carbohydrate amphiphiles aggregate into hierarchically organized micellar clusters of individual aggregates. The micellar clusters may be transformed into stable nanoparticles with drugs, especially hydrophobic drugs that have poor aqueous solubility, and may improve the transfer of hydrophobic drugs across biological barriers.

29 Claims, 8 Drawing Sheets

OTHER PUBLICATIONS

Jones, M.C. et al. "Polymeric micelles—a new generation of colloidal drug carriers" *European Journal of Pharmaceutics and Biopharmaceutics*, Sep. 1, 1999, 48(2): 101-111.

Torchilin, V.P. "Structure and design of polymeric surfactant-based drug delivery systems" *Journal of Controlled Release*, Jun. 15, 2001, 73(2-3): 137-172.

Savić, R. et al. "Micellar Nanocontainers Distribute to Defined Cytoplasmic Organelles" *Science*, Apr. 25, 2003, 300(5619): 615-618.

Francis, M.F. et al. "Solubilization of cyclosporin A in dextran-g-polyethyleneglycolalkyl ether polymeric micelles" *European Journal of Pharmaceutics and Biopharmaceutics*, Nov. 2003, 56(3): 337-346.

Uchegbu, I.F. et al. "Quaternary ammonium palmitoyl glycol chitosan—a new polysoap for drug delivery" *International Journal of Pharmaceutics*, Aug. 14, 2001, 224(1-2): 185-199.

Miwa, A. et al. "Development of Novel Chitosan Derivatives as Micellar Carriers of Taxol" *Pharmaceutical Research*, Dec. 15, 1998, (12): 1844-1850.

Wang, W. et al. "Self-Assembly of Cetyl Linear Polyethylenimine to Give Micelles, Vesicles, and Dense Nanoparticles" *Macromolecules*, Nov. 30, 2004, 37(24): 9114-9122.

Wang, W. et al. "Controls on Polymer Molecular Weight May Be Used to Control the Size of Palmitoyl Glycol Chitosan Polymeric Vesicles" *Langmuir*, Feb. 6, 2001, 17(3): 631-636.

Discher, D.E. et al. "Polymer Vesicles" *Science*, Aug. 9, 2002, 297(5583): 967-973.

Wang, W. et al. "A New Class of Amphiphilic Poly-L-lysine Based Polymers Forms Nanoparticles on Probe Sonication in Aqueous Media" *Langmuir*, Oct. 3, 2000, 16(20): 7859-7866.

Gref, R. et al. "Biodegradable Long-Circulating Polymeric Nanospheres" *Science*, Mar. 18, 1994, 263(5153): 1600-1603.

Wang, G.J. et al. "Synthesis and Catalytic Properties of Cross-Linked Hydrophobically Associating Poly(alkylmethyldiallylammonium bromides)".*The Journal of Organic Chemistry*, Jul. 1994, 59(15): 4076-4081.

Yoshioka, H. et al. "Chitosan-derived Polymer-surfactants and Their Micellar Properties" *Bioscience, Biotechnology, and Biochemistry*, 1995, 59(10): 1901-1904.

Kabanov, A.V. et al. "A new class of drug carriers: micelles of poly(oxyethylene)-poly(oxypropylene) block copolymers as microcontainers for drug targeting from blood in brain" *Journal of Controlled Release*, Oct. 1992, 22(2):141-157.

Yu, B.G. et al. "Polymeric micelles for drug delivery: solubilization and haemolytic activity of amphotericin B" *Journal of Controlled Release*, Apr. 30, 1998, 53(1-3): 131-136.

Akiyoshi, K. et al. "Self-Aggregates of Hydrophobized Polysaccharides in Water. Formation and Characteristics of Nanoparticles" *Macromolecules*, Jun. 1993, 26(12): 3062-3068.

Rekatas, C.J. et al. "The effect of hydrophobe chemical structure and chain length on the solubilization of griseofulvin in aqueous micellar solutions of block copoly(oxyalkylene)s" *Physical Chemistry Chemical Physics*, 2001, 3(21): 4769-4773.

Dwyer, C. et al. "Propofol induced micelle formation in aqueous block copolymer solutions" *Colloids and Surfaces A: Physiochemical and Engineering Aspects*, Mar. 10, 2005, 254(1): 23-30.

Kim, S.Y. et al. "Taxol-loaded block copolymer nanospheres composed of methoxy poly(ethylene glycol) and poly(ε-caprolactone) as novel anticancer drug carriers" *Biomaterials*, Jul. 2001, 22(13): 1697-1704.

Francis, M.F. et al. "Solubilization of poorly water soluble drugs in micelles of hydrophobically modified hydroxypropylcellulose copolymers" *Journal of Controlled Release*, Nov. 18, 2003, 93(1): 59-68.

Kjøniksen, A.L. et al. "Viscosity of Dilute Aqueous Solutions of Hydrophobically Modified Chitosan and Its Unmodified Analogue at Different Conditions of Salt and Surfactant Concentrations" *Langmuir*, Sep. 17, 1997, 13(19): 4948-4952.

Philippova, O.E. et al. "Two Types of Hydrophobic Aggregates in Aqueous Solutions of Chitosan and Its Hydrophobic Derivative" *Biomacromolecules*, Jun. 2001, 2(2): 483-490.

Noble, L. et al. "A non-covalently cross-linked chitosan based hydrogel" *International Journal of Pharmaceutics*, Dec. 10, 1999, 192(2): 173-182.

Wakita, M. et al. "Bilayer Vesicle Formation of N-Octadecylchitosan" *Kobunshi Ronbunshu*, Oct. 1995, 52(10): 589-593.

Uchegbu, I.F. et al. "Polymeric Chitosan-based Vesicles for Drug Delivery" *Journal of Pharmacy and Pharmacology*, May 1998, 50(5): 453-458.

Lee, K.Y. et al. "Physiochemical Characteristics of Self-Aggregates of Hydrophobically Modified Chitosans" *Langmuir*, Apr. 28, 1998, 14(9): 2329-2332.

Kwon, S. et al. "Physicochemical Characteristics of Self-Assembled Nanoparticles Based on Glycol Chitosan Bearing 5β-Cholanic Acid" *Langmuir*, Nov. 25, 2003, 19(24): 10188-10193.

Hughes, P.M. et al. "Topical and systemic drug delivery to the posterior segments" *Advanced Drug Delivery Reviews*, Dec. 13, 2005, 57(14): 2010-2032.

Langley, M.S. et al. "Propofol: A Review of its Pharmacodynamic and Pharmacokinetic Properties and Use as an Intravenous Anaesthetic" *Drugs*, Apr. 1988, 35(4): 334-372.

Dutta, S. et al. "Formulation-dependent Pharmacokinetics and Pharmacodynamics of Propofol in Rats" *Journal of Pharmacy and Pharmacology*, Jan. 1998, 50(1): 37-42.

Furusaki, E. et al. "Facile preparation and inclusion ability of a chitosan derivative bearing carboxymethyl-β-cyclodextrin" *Carbohydrate Polymers*, Jan. 1996, 29(1): 29-34.

Griffin, W.C. "Classification of Surface-Active Agents by "HLB"" *Journal of Cosmetic Science*, Dec. 1949, 1(5): 311-326.

Kan, P.L. et al. "Highly Hydrophilic Fused Aggregates (Microsponges) from a C12 Spermine Bolaamphiphile" *Journal of Physical Chemistry B*, Jun. 17, 2004, 108(24): 8129-8135.

Rocci, M.L. et al. "Analysis of Prednisone, Prednisolone and their 20β-hydroxylated metabolites by high-performance liquid chromatography" *Journal of Chromatography*, Jul. 10, 1981, 224(2): 221-227.

Florence, A.T. et al., *Physicochemical Principles of Pharmacy*, Fourth edition, 1998, Basingstoke: Macmillan Press.

International Search Report in International Application No. PCT/GB2007/003016, filed Aug. 8, 2007.

* cited by examiner

Polymer Micelle Cluster

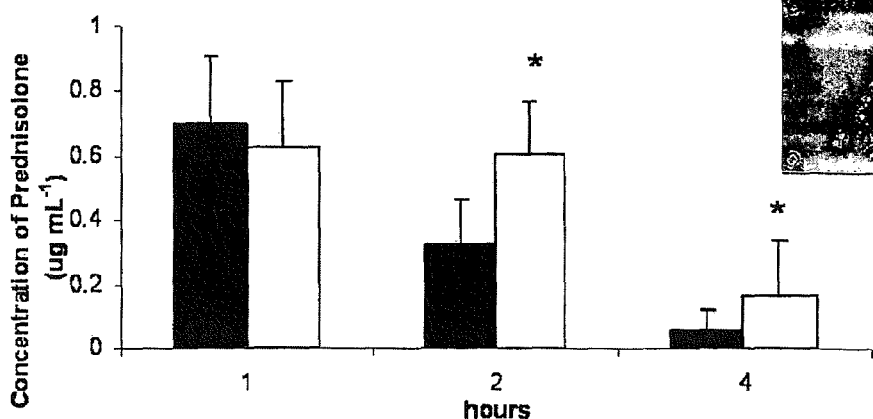
Fig. 4A
Fig. 4B
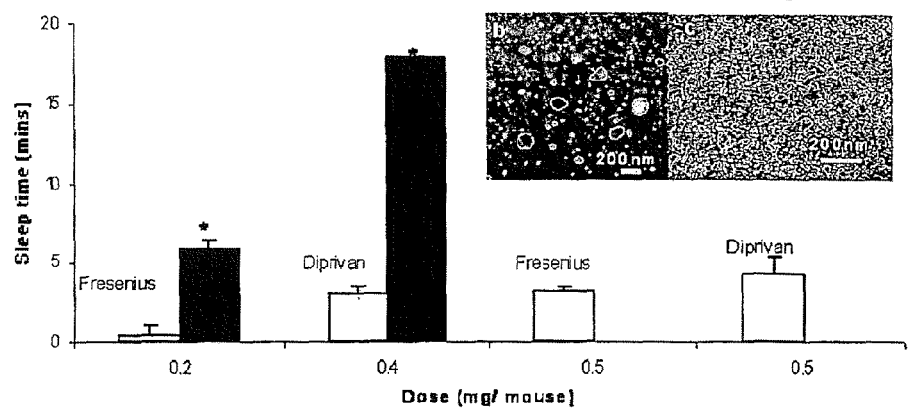
Fig. 5A
Fig. 5B
Fig. 5C

US 8,470,371 B2

POLYMERIC MICELLAR CLUSTERS AND THEIR USES IN FORMULATING DRUGS

FIELD OF THE INVENTION

The present invention relates to polymeric micellar clusters formed from amphiphilic carbohydrate polymers and their uses in formulating drugs, in particular drugs that are poorly soluble.

BACKGROUND OF THE INVENTION

The combination of both polar and apolar segments in a molecule allows the manipulation of immiscible liquids in a manner that is applicable to a wide variety of processes: ranging from the use of detergents for environmental clean up activities to the processing of foods. In the pharmaceutical industry, the formulation of drugs that are immiscible with water is often fraught with failure [1, 2] despite the availability of amphiphilic compounds with approved excipient status [3]. However, ensuring sufficient bioavailability from drugs with poor aqueous solubility, i.e. hydrophobic drugs, is of great importance in drug development. Drugs with poor aqueous solubility are defined by the British Pharmacopoeia as "very slightly soluble" and such drugs have an aqueous solubility of less than 1 mg per milliliter of solvent (Medicines Commission, British Pharmacopoeia, The Stationary Office, London, 2002)

Bioavailability of hydrophobic drugs has been improved in the past by the addition of block copolymers [14-18]. It is known that both block copolymer and grafted polymer amphiphiles self assemble into polymeric micelles [5, 22], vesicles [23, 24] and dense amorphous nanoparticles [22, 25, 26]. Block copolymer micelles are conventional single micelle entities with a diameter of 12-36 nm [29, 30].

Micellar phases have been used to solubilise drugs in aqueous media and the stability of the drug solubilising micellar core, according to the phase separation model is a function of its critical micellar concentration (CMC, Equation 1)—the concentration at which micellar aggregates begin to form.

$$\Delta G_{micelle}^0 = RT \ln X_{cmc}$$

where $\Delta G_{micelle}^0$=the standard free energy of micellisation, R=the gas constant, T=temperature and $X_{cmc}$=the critical micelle concentration in mole fraction units. A lower CMC thus favours micellisation.

Pharmaceutically approved low molecular weight surfactants [4] and block copolymers [5-7] typically possess CMC values in the mM concentration range and are inefficient in carrying hydrophobic drugs as molar amphiphile/drug ratios are typically in excess of 10:1 and frequently extend to 1000:1 [4, 8-10]. The solubilisation of drugs within micellar cores for a fixed mole of solubilising micelle is dependent on the log P of the solubilisate [11], molecular volume of the solubilisate [11] and relative size of the hydrophobic nanodomain formed by the association colloid [12, 13]. A high log P/molar volume ratio favours partitioning into micelles and a large hydrophobic volume within the micelle favours the encapsulation of drugs within the micelle.

Increasing the hydrophobic volume of a particle by increasing the aggregation number of the individual monomers to yield larger particles is thus a possible means of increasing the level of drug that may be solubilised within colloidal aggregates. However care must be taken to avoid excessive aggregation which would lead to precipitation of the colloid forming molecules and the drug.

Previously, we have disclosed solubilising carbohydrate polymers and shown that they can be employed to formulate hydrophobic drugs which are added to an aqueous phase in the presence of the solubilising carbohydrate polymers (WO 04/026912). In the exemplified amphiphilic polymers disclosed in this application, the molar percentage of palmitoyl groups was between 3.0% and 8.2% and the molar percentage of, quaternary ammonium groups was between 7.9% and 19.0%.

However, there remains a continuing need in the art for further ways to formulate drugs to improve their delivery, in particular to increase the bioavailability of hydrophobic drugs.

SUMMARY OF THE INVENTION

Broadly, the present invention is based on the unexpected finding that amphiphilic carbohydrate polymers are capable of self assembling to form micellar clusters in which the carbohydrate amphiphiles aggregate into hierarchically organised micellar clusters of individual aggregates. These micellar clusters formed by the aggregation of individual micelles may be contrasted with the individual micelles that were produced using the polymers and conditions described in WO 2004/026912. The present invention discloses that these micellar clusters may be transformed into stable nanoparticles with drugs, especially hydrophobic drugs that have poor aqueous solubility. In preferred embodiments, this helps to provide molar polymer/drug ratios that are greater than the ratios observed with the prior art use of the Pluronic block copolymers. Finally, the present invention also demonstrates that drug formulations formed from the micellar clusters may improve the transfer of hydrophobic drugs across biological barriers by an order of magnitude.

Accordingly, in a first aspect, the present invention provides a polymeric micellar aggregate having a mean particle size between 20 nm and 500 nm formed from an amphiphilic carbohydrate polymer, wherein the carbohydrate polymer is a derivatised chitosan comprising a plurality of linked monomer units and wherein (i) amine groups of a first portion of the monomer units are derivatised with a hydrophobic group and (ii) amine groups of a second portion of the monomer units are derivatised to provide a group possessing a quaternary ammonium group, such as a —$N^+R_1R_2R_3$ group, where each R group may be hydrogen or a functional group as described below. Optionally, the derivatised chitosan polymer may comprise a third portion of monomer units in which the amines are derivatised in a different manner to the first or second group or are underivatised. Additionally or alternatively, the —$CH_2$—OH groups present on the C6 atoms of the first and/or second and/or third portions of the monomer units may be derivatised, for example by reacting one or more of these hydroxyl groups of the chitosan monomer units to form O-linked groups such as an ether.

More specifically, the present invention provides a polymeric micellar aggregate having a mean particle size between 20 nm and 500 nm formed from an amphiphilic carbohydrate polymer, wherein the carbohydrate polymer is represented by the general formula:

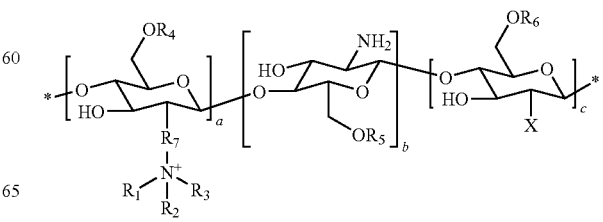

wherein a+b+c=1.000 and
a is between 0.010 and 0.990,
b is between 0.000 and 0.980, and
c is between 0.010 and 0.990;
and wherein substituents $R_1$ to $R_7$ and X are as defined below.

In the above general formula, the a, b and c units may be arranged in any order and may be ordered, partially ordered or random. The * in the formula is used to indicate the continuing polymer chain. In preferred embodiments, the derivatised carbohydrate polymers employed in the present invention have higher proportions of hydrophobic groups compared to the polymers disclosed in the prior art. In preferred embodiments, the molar proportion of the c units is greater than 0.100, and more preferably is at least 0.110, more preferably is at least 0.120, more preferably is at least 0.150, more preferably is at least 0.180, more preferably is at least 0.200 or in some embodiments is at least 0.250. Generally, the molar proportion of the c unit is 0.400 or less, and more preferably is 0.350 or less.

Preferably, the molar proportions of the a unit is between 0.050 and 0.800, and more preferably between 0.100 and 0.400.

Preferably, the molar proportions of the b unit is between 0.200 and 0.850, and more preferably between 0.200 and 0.750.

As can be seen from the above formula, the b units may optionally be absent. The c units provide the first portion of the monomer units that are derivatised with a hydrophobic group, and the a units provide the second portion of the monomer units are derivatised with a quaternary nitrogen group. When present, the b units provide the third group of monomer units in which the amine groups are derivatised in a different manner to the first or second group, or else are underivatised.

In the present invention, the hydrophobic group X is preferably selected from a substituted or unsubstituted group which is an alkyl group such as a $C_{4-30}$ alkyl group, an alkenyl group such as a $C_{4-30}$ alkenyl group, an alkynyl group such as a $C_{4-30}$ alkynyl group, an aryl group such as a $C_{5-20}$ aryl group, a multicyclic hydrophobic group with more than one $C_4$-$C_8$ ring structure such as a sterol (e.g. cholesterol), a multicyclic hydrophobic group with more than one $C_4$-$C_8$ hetero atom ring structure, a polyoxa $C_1$-$C_4$ alkylene group such as polyoxa butylene polymer, or a hydrophobic polymeric substituent such as a poly(lactic acid) group, a poly(lactide-co-glycolide) group or a poly(glycolic acid) group. The X groups may be linear, branched or cyclo groups. Any of the X groups may be directly linked to the c unit (i.e. at the C3) or via a functional group such as an amine group, an acyl group or an amide group, thereby forming linkages that may be represented as X'-ring, X'—NH—, X'—CO-ring, X'—CONH-ring, where X' is the hydrophobic group as defined above.

Preferred examples of X groups include those represented by the formulae $CH_3(CH_2)_n$—CO—NH— or $CH_3(CH_2)_n$—NH— or the alkeneoic acid $CH_3(CH_2)_p$—CH=CH—$(CH_2)_q$—CO—NH—, where n is between 4 and 30, and more preferably between 6 and 20, and p and q may be the same or different and are between 3 and 15, and more preferably 5 and 10. A particularly preferred class of X substituents are linked to the chitosan monomer unit via an amide group, for example as represented by the formula $CH_3(CH_2)_n$CO—NH—, where n is between 4 and 30. Examples of amide groups are produced by the coupling of carboxylic acids to the amine group of chitosan. Preferred examples are fatty acid derivatives such as those based on lauric acid (n=10), myristic acid (n=12), palmitic acid (n=14), stearic acid (n=16) or arachidic acid (n=18).

In the above formula, $R_1$, $R_2$ and $R_3$ are preferably independently selected from hydrogen or a substituted or unsubstituted alkyl group such as a $C_{1-10}$ alkyl group. Where $R_1$, $R_2$ and/or $R_3$ are alkyl groups, they may be linear or branched. Preferably, $R_1$, $R_2$ and $R_3$ are independently selected from hydrogen, methyl, ethyl or propyl groups.

In the above formula, $R_4$, $R_5$ and $R_6$ present on the C6 of the sugar units are independently selected from hydrogen, a substituted or unsubstituted alkyl group, a substituted or unsubstituted ether group, or a substituted or unsubstituted alkene group. Preferred $R_4$, $R_5$ and $R_6$ groups are substituted with one of more hydroxy groups, or another non-ionic hydrophilic substituent. Examples of $R_4$, $R_5$ and $R_6$ groups are represented by the formulae —$(CH_2)_p$—OH, where p is between 1 and 10, and is preferably between 2 and 4, or —$(CH_2)_p$—$CH_q(CH_2\_OH)_r$, where p is between 1 and 10, and q is between 0 and 3 and r is between 1 and 3 and the sum of q+r=3, or —$(CH_2)_p$—$C(CH_2\_OH)_r$, where p is between 1 and 10, and r is 3, or —$(CH_2CH_2OH)p$, where p is between 1 and 300.

The $R_7$ group may be present or absent in the general formula. When absent, it provides a quaternary ammonium functional group that is directly linked to the chitosan ring of the a monomer unit. When the $R_7$ group is present it may be a unsubstituted or substituted alkyl group (e.g. a $C_{1-10}$ alkyl group) for example as represented by the formula —$(CH_2)_n$—, an amine group as represented by the formula —NH—$(CH_2)_n$—, or an amide group as represented by the formula —NH—CO—$(CH_2)_n$—, where n is 1 to 10 and is preferably 1 to 4. A preferred example of the $R_7$—$N^+R_1R_2R_3$ substituent is provided by coupling betaine ($^-OOC$—$CH_2$—$N^+(CH_3)_3$) to the amine substituent of the a unit providing an amide group such as in betaine, —NH—CO—$CH_2$—$N^+R_1R_2R_3$.

As indicated, some of the substituents described herein may be either unsubstituted or substituted with one or more additional substituents as is well known to those skilled in the art. Examples of common substituents include halo; hydroxy; ether (e.g., $C_{1-7}$alkoxy); formyl; acyl (e.g., $C_{1-7}$alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., unsubstituted $C_{1-7}$alkyl, $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; and $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)) groups.

The term "ring structure" as used herein, pertains to a closed ring of from 3 to 10 covalently linked atoms, more preferably 3 to 8 covalently linked atoms, yet more preferably 5 to 6 covalently linked atoms. A ring may be an alicyclic ring, or aromatic ring. The term "alicyclic ring," as used herein, pertains to a ring which is not an aromatic ring.

The term "carbocyclic ring", as used herein, pertains to a ring wherein all of the ring atoms are carbon atoms.

The term "carboaromatic ring", as used herein, pertains to an aromatic ring wherein all of the ring atoms are carbon atoms.

The term "heterocyclic ring", as used herein, pertains to a ring wherein at least one of the ring atoms is a multivalent ring heteroatom, for example, nitrogen, phosphorus, silicon, oxygen or sulphur, though more commonly nitrogen, oxygen, or sulphur. Preferably, the heterocyclic ring has from 1 to 4 heteroatoms.

The above rings may be part of a "multicyclic group".

As discussed above, the polymeric micellar aggregates of the present invention are formed by the aggregation of individual micelles and have a mean particle size between 20 nm and 500 nm. The mean particle size can readily be determined microscopically or by using photon correlation spectroscopy and is conveniently determined in aqueous solution prior to filtration. More preferably, the polymeric micellar aggregates have a minimum mean particle size of at least 100 nm, and more preferably at least 175 nm, and a maximum mean particle size which is preferably 400 nm or less. After filtration, the mean particle size typically reduces to a preferred range between about 100 nm and 250 nm, see for example, Table 1.

As disclosed in the protocol in the examples, the carbohydrate polymer used is depolymerised to produce the polymer that is then derivatised, for example to include the hydrophobic groups and the quaternary ammonium groups. Preferably, carbohydrate polymer has a molecular weight between about 1.5 kDa and about 250 kDa, more preferably between about 1.5 kDa and 100 kDa and more preferably between about 2 kDa and about 25 kDa.

In further embodiments, the polymeric micellar aggregates of the present invention have a hydrophobicity index (HI) of between about 0.5 to 6, and more preferably between about 0.8 to 4.4, as determined by using $^1$H nuclear magnetic resonance (NMR) spectrometry to measure the molar level of hydrophobic substituents and the molar level of hydrophilic (quaternary ammonium) substituents on the carbohydrate; where $$HI = \frac{Q}{L},$$

where Q=molar fraction of quaternary ammonium groups per monomer and L=molar fraction of hydrophobic groups per monomer.

Those skilled in the art will also recognise the fact that polymer synthesis and derivatisation reactions are not exact. As a result, there will be variations within any given sample of a polymer both with regard to the size of the polymer, the molar proportions of the a, b and c monomer units present in a polymer and the arrangement of the a, b and c monomer units within each polymer within the sample. Hence, the possible ranges and values given above represent averages over a polymer sample as a whole. In addition, the order of the different types of monomer units in the polymer may be ordered in a regular pattern or as a block copolymer or may be random.

In addition, where the polymers are charged, they include one or more counter ions. Typically, this is a result of the quaternary ammonium groups present in the polymer and the counter ion will be a negatively charged ion such as chloride, iodide, acetate or glutamate ions. The polymers and compositions provided herein may also be in the form of a salt, such as a pharmaceutically acceptable salt.

In a further aspect, the present invention provide a composition comprising a polymeric micellar aggregate defined above. Preferred compositions include pharmaceutical compositions formed from the polymeric micellar aggregates as defined herein and a drug, more preferably a hydrophobic drug. In a preferred embodiment, in the pharmaceutical compositions, the polymeric micellar aggregates form nanoparticles with the drug molecule, the nanoparticles having mean diameters between about 20 nm and about 2 μm, and more preferably between about 20 nm and 200 nm.

In preferred embodiments, the present invention provides advantageously high molar ratios of polymer/drug compared to the prior art of at least 1:10, more preferably at least 1:20 and most preferably at least 1:40. Conveniently, drugs may be loaded to form the nanoparticles by a homogenization method such as sonication and mixing or high pressure homogenization.

Examples of hydrophobic drugs include prednisolone, propofol, cyclosporine, oestradiol, testosterone, drugs with multicyclic ring structures which lack polar groups such as paclitaxel and drugs such as etoposide, amphotericin B, steroids and other multicyclic compounds.

In a further aspect, the present invention provides a pharmaceutical composition as defined herein for use in therapy.

In a further aspect, the present invention provides the use of a polymeric micellar aggregate as defined herein and a drug for the preparation of a medicament for delivery of the drug to a patient. In preferred embodiments the drug is poorly soluble in water.

Embodiments of the present invention will now be described by way of example and not limitation with reference to the accompanying figures.

BRIEF DESCRIPTION OF THE FIGURES

FIG. 4a: Prednisolone concentrations (mean±s.d.) in the aqueous humour of rabbits dosed with either Prednisolone Forte (white bar, prednisolone acetate suspension, 10 mg mL$^{-1}$, 35 μL, Allergan, USA) or a GCPQ (quaternary ammonium palmitoyl glycol chitosan) formulation of prednisolone (black bar, G2—1 mg mL$^{-1}$, NaHCO$_3$—0.01M, prednisolone—1 mg mL$^{-1}$, 35 µL)*=statistically significant difference (p<0.05, n=4).

FIG. 4b: negative stained transmission electron micrograph of prednisolone formulation.

FIG. 5a: Pharmacodynamic activity (sleep time, mean±s.d., n 4) of propofol formulations after tail vein dosing to male MF1 mice. Mice were dosed as described below. i) 0.2 mg animals were dosed with 0.2 mg propofol in a 100 µL volume administered as either propofol emulsion (10 mg mL$^{-1}$, Fresenius, Germany) diluted to 2 mg mL$^{-1}$ with phosphate buffered saline (PBS, pH=7.4) or a filtered GCPQ formulation (G19—5 mg mL-1, propofol 1.9 mg mL-1 in PBS—pH=7.4). ii) 0.4 mg animals were dosed with 0.4 mg of propofol in a 100 µL volume administered as either Diprivan diluted in glycerol (0.24 M-TEM of formulation shown in FIG. 5b) to a concentration of 4 mg mL$^{-1}$ or a filtered GCPQ formulation of propofol (G41—5 mg mL$^{-1}$, propofol—4.2 mg ml-1, lecithin 2 mg mL$^{-1}$, in glycerol—0.24 M-TEM of formulation shown in FIG. 5c). iii) 0.5 mg animals were dosed with 0.5 mg propofol administered in a 50 µL volume as either Diprivan (10 mg mL-1) or propofol emulsion (Fresenius, 10 mg mL-1). A loss of righting reflex time was only observed in animals receiving a low dose of the commercial emulsion formulations (0.37±0.19 min in the 0.2 Fresenius animals). No sleep times were recorded in animals receiving the polymer alone. *=statistically significantly different (p<0.05).

DETAILED DESCRIPTION

Hydrophobic Drugs

Figure 1:
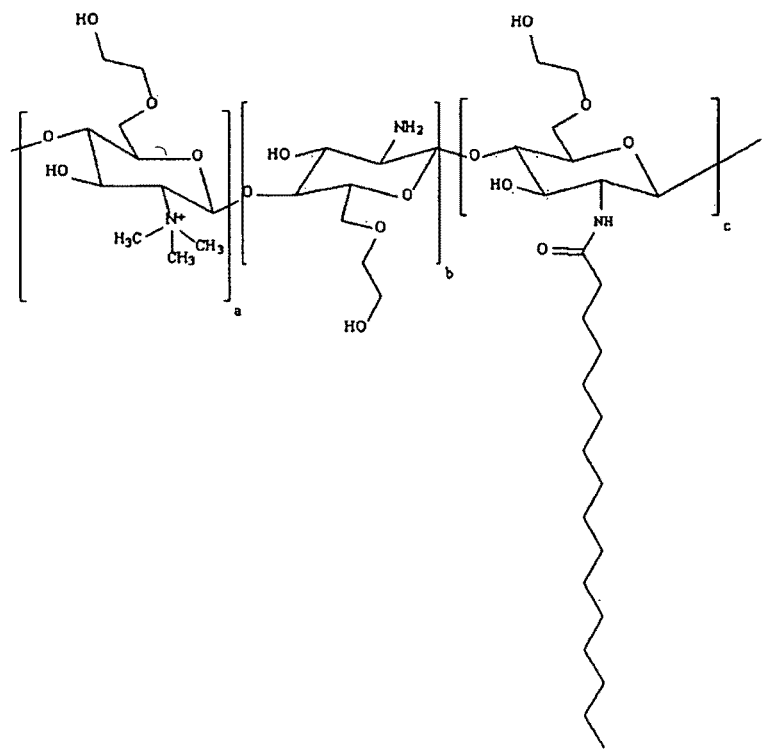
FIG. 1: A schematic structure of a quaternary ammonium palmitoyl glycol chitosan.

The micellar polymeric aggregates of the present invention may be used to solubilise drugs and in particular hydrophobic drugs. The term "hydrophobic drug" as used herein includes drugs which are very slightly soluble in water. The definition of "very slightly soluble" is used by the British Pharmacopoeia and is defined as a situation where 1 g of such material requires more than 1,000 milliliters of solvent (e.g. water) to be solubilised or alternatively a material which has a solubility of less than 1.0 mg mL$^{-1}$ in water.

Examples of hydrophobic drugs include prednisolone, propofol, cyclosporine, oestradiol, testosterone, drugs with multicyclic ring structures which lack polar groups such as paclitaxel and drugs such as etoposide, amphotericin B, steroids and other multicyclic compounds. Preferred hydrophobic drugs include prednisolone, propofol or cyclosporine. Prednisolone is a synthetic adrenal corticosteroid and is used, for example, as an ocular anti-inflammatory drug. Propofol is a short-acting intravenous anesthetic agent used for the induction of general anesthesia in adult patients and pediatric patients older than 3 years of age; maintenance of general anesthesia in adult patients and pediatric patients older than 2 months of age; and intensive care unit sedation for intubated, mechanically ventilated adults. Cyclosporine (also known as ciclosporin or cyclosporin), is an immunosuppressant drug. It is widely used post-allogeneic organ transplant to reduce the activity of the patient's immune system and so the risk of organ rejection. It has been studied in transplants of skin, heart, kidney, lung, pancreas, bone marrow and small intestine. Cyclosporine is a cyclic nonribosomal peptide of 11 amino acids (an undecapeptide) produced by the fungus *Hypocladium inflatum gams*.

Delivery Routes and Pharmaceutical Formulations

The pharmaceutical compositions may be delivered by a range of delivery routes including, but not limited to: gastrointestinal delivery, including orally and per rectum; parenteral delivery, including injection, patches, creams etc; mucosal delivery, including nasal, inhalation and via pessary. In a preferred embodiment, the pharmaceutical compositions are administered via parenteral, oral or topical routes.

In addition to the polymeric micellar aggregates and drugs as described above, the pharmaceutical compositions may comprise a pharmaceutically acceptable excipient, carrier, diluent, buffer, stabiliser or other materials well known to those skilled in the art. Such materials should be non-toxic and should not interfere with the efficacy of the composition. The precise nature of the carrier or other material may depend on the route of administration, e.g. parenteral, oral or topical routes. Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride for injection. Preservatives, stabilisers, buffers, antioxidants and/or other additives may be included, as required.

EXPERIMENTAL

Introduction

The present invention is based on the surprising finding that carbohydrate amphiphiles aggregate into a hierarchically organised micellar clusters of individual aggregates and that these micellar clusters transform to stable nanoparticles with molar polymer/hydrophobic drug ratios as high as 1:67 (drug/polymer weight ratios as low as 0.8:1) which is 20 times the level seen with the Pluronic triblock block copolymers.

In addition, these micellar clusters improve the transfer of hydrophobic drugs across biological barriers by an order of magnitude.

The micellar clusters formed by the amphiphilic carbohydrate polymers are distinct from the micelles [5, 22], vesicles [23, 24] and dense amorphous nanoparticles [22, 25, 26] previously described for block copolymers and grafted polymer amphiphiles. This can be deduced, for example, from the fact that the size of the micellar clusters ranges from 100-400 nm prior to filtration and 100-300 nm in size post filtration (45 µm). In contrast, the diameter of the conventional single micelle entities formed by block copolymers, for example, is 12-36 nm [29, 30] and cholesteryl pullulans are also believed to exist as single micelles with a diameter of 25 nm [31].

The micellar clusters consist of smaller 10-30 nm aggregates and the nanopolarity of their hydrophobic domains and drug incorporation efficiency can be tailored by varying the degree of lipidic derivatisation and molecular weight of the carbohydrate.

On intravenous injection of a carbohydrate propofol formulation, the pharmacodynamic activity of the model drug is increased by an order of magnitude when compared to a commercial coarse emulsion formulation and on topical ocular application of a carbohydrate prednisolone formulation, the initial levels of drug found in the aqueous humour are similar to those found with a ten fold dose of prednisolone suspension. Hence, these novel polymer micellar clusters can be used to increase the bioavailability of hydrophobic drugs Higher levels of drugs with limited or no aqueous solubility have to be administered than are necessary for drugs with higher aqueous solubility. Therefore, provision of carrier compounds which increase the bioavailability of drugs with limited or no aqueous solubility are of paramount importance in the pharmaceutical industry. One advantage of such carrier compounds is that they reduce the amount of a drug with limited or no aqueous solubility that must be administered to an animal in order to treat a given medical condition.

Materials and Methods

Synthesis of quaternary ammonium palmitoyl glycol chitosan

Quaternary ammonium palmitoyl glycol chitosan (GCPQ) samples were synthesised using a modification of the method previously reported [20], as described below. All reagents were used as received and supplied by Sigma Aldrich, Co. UK, unless otherwise stated. Organic solvents were supplied by the Department of Pure and Applied Chemistry, University of Strathclyde. Glycol chitosan (GC—Mw~250 kDa) with a degree of acetylation below the level of detection using $^1$H NMR (signal at 2 ppm) was degraded for 48 h by heating at 50° C. in a solution of hydrochloric acid (4 M) [23] to give 10-15 kDa GC samples. Alternatively, 4 kDa GC samples were prepared by adapting a previously published method of GC degradation [47]. GC (Mw~250 kDa, 1 g) was dissolved in acetic acid (2.5% v/v, 50 mL). Dissolved oxygen was removed by bubbling $N_2$ gas through the solution for 5 min. After cooling to 0-4° C., a freshly prepared solution of $NaNO_2$ (9.5 mg mL$^{-1}$, 2 mL) was added, and the reaction was allowed to proceed for 15 h at 4° C. in the dark and without stirring. The product was neutralised with concentrated aqueous ammonia. To the resulting mixture was added $NaBH_4$ (20 mg) in divided portions and the reaction mixture was once again left stirring overnight at room temperature. At the end of this period the product was carefully precipitated by adding acetone (150 mL) at room temperature. The resulting precipitate was separated by centrifugation (9,000 g×10 min), washed three times with methanol (50 mL), redissolved in water, dialyzed exhaustively as described below and the dialysate freeze dried. The yield was 400 mg.

Degraded GC (300 mg) was dissolved in a sodium bicarbonate solution (0.057M), a solution of palmitic acid N-hydroxysuccinimide (120 mL) added at the level given in Table 1 and the mixture stirred for 72 h. Ethanol was removed by evaporation under reduced pressure and the reaction mixture extracted with diethyl ether (3×100 mL). The crude palmitoyl glycol chitosan (PGC) was dissolved in an N-methylpyrrolidone solution of sodium iodide (0.011M, 90 mL) by stirring overnight and to this solution was added an ethanolic solution of sodium hydroxide (0.25 M, 18 mL) and methyl iodide at the level indicated in Table 1. The mixture was stirred under nitrogen gas at 36° C. for 4 h, the product precipitated in diethyl ether (400 mL) and washed twice with diethyl ether (2×300 mL). Finally the product was dissolved in water (100 mL) and dialysed exhaustively against an aqueous sodium chloride solution (0.1M, 5 L) to give a protonated polymer (chitosan pKa ~7) or an aqueous solution (5 L) containing sodium bicarbonate (0.01 M) and sodium chloride (0.1M); the latter giving a deprotonated polymer. Both dialysis media described above were changed 3 times (over 4.5 h) and followed by dialysis against water (5 L) with 6 changes (over 24 h). The synthetic yield for all polymers was ~120 mg. Protonated and deprotonated versions of G19 were prepared. All other polymers were dialysed against water (5 L with 6 changes over 24 h) and passed through an ion exchange column equilibrated with chloride ions (IRA 93 Cl-1) [20] prior to freeze drying.

The molecular weight of degraded GC was determined by gel permeation chromatography-multi-angle laser light scattering [23] and the level of both palmitoylation and methylation determined by $^1$H NMR by comparing the palmitoyl methyl protons (0.8 ppm, palmitoyl) and the quaternary ammonium methyl protons (3.35 ppm, quaternary ammonium glycol chitosan) respectively with the sugar methine protons (3.1 and 3.5-5.5 ppm) [20]. The Hydrophobicity Index (HI) was calculated using equation 2:

$$HI = \frac{Q}{L} \qquad 2$$

where Q=molar fraction of quaternary ammonium groups per monomer and L=molar fraction of palmitoyl groups per monomer) and an approximation of the HLB [4, 48] made using equation 3:

$$HLB = \frac{M_1Q + \{M_2[1-(Q+L)]\} + M_3L}{M_4L + M_1Q + \{M_2[1-(Q+L)]\} + M_3L}\left(\frac{100}{5}\right) \qquad 3$$

where $M_1$=molecular weight of quaternary ammonium sugar monomer, $M_2$=molecular weight of amino sugar monomer, $M_3$=molecular weight of $CH_3CO$— amino sugar monomer, $M_4$=molecular weight of tetradecyl moiety.

Polymer Aggregation and Drug Encapsulation

Methyl orange serves as a solvatochromic probe by undergoing a hypsochromic shift of its long wavelength band on movement from a polar to a non polar domain [22, 27], such as that resulting from polymer aggregation [22]. Alkaline solutions of methyl orange were used to probe for polymer aggregation, by measuring the degree of the hypsochromic shift with increase in polymer aqueous concentration [22]. The CMC was taken as the first inflection point in the methyl orange wavelength of maximum absorbance-concentration curve. GCPQ NMR and GC GPC-MALLS data were used to calculate the molecular weight of the polymers in order to obtain molar CMC data. Photon correlation spectroscopy was used to record aggregate size before and after filtration (0.45 µm) [25] and both freeze fracture electron microscopy [49] and negative stained transmission electron microscopy [23] used to record images of the aggregates.

Drug loading on the aggregates was achieved by probe sonicating [25] a mixture of the drug and the polymer in aqueous media. Drug levels contained in the aggregates were measured after filtration of the aggregates (0.45 μm) and analyses by high performance liquid chromatography (HPLC). For prednisolone: polymer/drug samples were filtered, diluted with the mobile phase (water/acetonitrile 640 mL: 360 mL) and chromatographed (20 μL) over a reverse phase 3.5 μm C18 column Symmetry (4.6×75 mm, Waters Instruments, UK) at a mobile phase flow rate of 1 mL min$^{-1}$. Chromatography was achieved using a Waters 515 isocratic pump, a Waters 717 autosampler and sample detection was achieved using a Waters 486 variable wavelength ultraviolet wavelength detector (λ=243 nm). The internal standard was 6α-methyl prednisolone (50 ng mL$^{-1}$), the limit of detection was 5 ng mL$^{-1}$ and the linear peak area ratio-concentration curve over the range 10-250 ng mL$^{-1}$ had a correlation coefficient of 0.9991. For propofol: polymer/drug samples were filtered (0.45 μm), diluted with the mobile phase (water/, methanol 200 mL: 800 mL) and chromatographed (20 μL) over an ODS2 5 μm column (4.6×250 mm, Waters Instruments, UK), at a mobile phase flow rate of 1 mL min$^{-1}$ and using the same instrumentation as used above but with the wavelength set at 229 nm. The limit of detection was 0.25 μg mL$^{-1}$ and the linear peak area-concentration curve over the range 1-250 μg mL$^{-1}$ had a correlation coefficient of 0.9997.

Statistics

Statistical analysis was performed using the students' t-test; significant differences were indicated by a p value of less than 0.05.

Results

Synthesis of Carbohydrate Amphiphiles

Glycol chitosan (GC) samples of three molecular weights (Table 1), obtained by acid degradation, were used to prepare the amphiphilic polymers. Syntheses of quaternary ammonium palmitoyl glycol chitosan (GCPQ) samples (FIG. 1) were confirmed by $^1$H NMR [20] (0.90 ppm=CH$_3$-palmitoyl, 1.25 ppm=CH$_2$-palmitoyl, 1.60 ppm=CH$_2$-palmitoyl β to carbonyl, 2.25 ppm=CH$_2$-palmitoyl α to carbonyl, 3.02 ppm=CH$_3$ monomethyl and dimethyl amino, 3.12 ppm=CH—C2 unsubstituted glycol chitosan, 3.35 ppm=CH$_2$ trimethyl amino, 3.5-5.5 ppm=CH glycol chitosan). 13 different amphiphiles were prepared with various levels of palmitoylation and quaternisation (Table 1).

Coarse control on palmitoylation levels were achieved by controlling the feed ratio of palmitic acid N-hydroxysuccinimide (PNS), while methyl quaternary ammonium levels largely remained similar so long as gravimetric methyl iodide/GC ratios remained at 14.14 or below.

Self Assembly

Figure 2A:
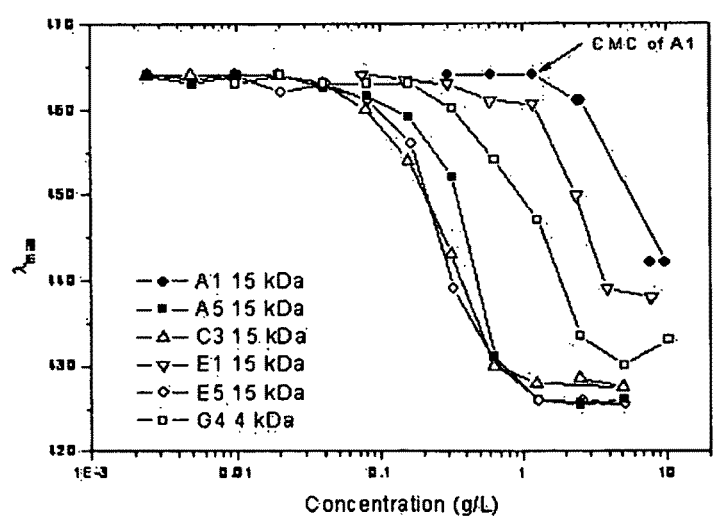
FIG. 2a: Effect of polymer hydrophobicity and molecular weight on polymer aggregation as probed by measuring the hypsochromic shift in methyl orange solutions. On location within an apolar environment methyl orange undergoes a hypsochromic shift. Polymer CMC is determined as the first inflexion point (arrowed for A1). For polymer details: hydrophobicity index (HI), approximated hydrophobic lipophilic balance (HLB) and CMC values see Table 1.
Figure 2B:
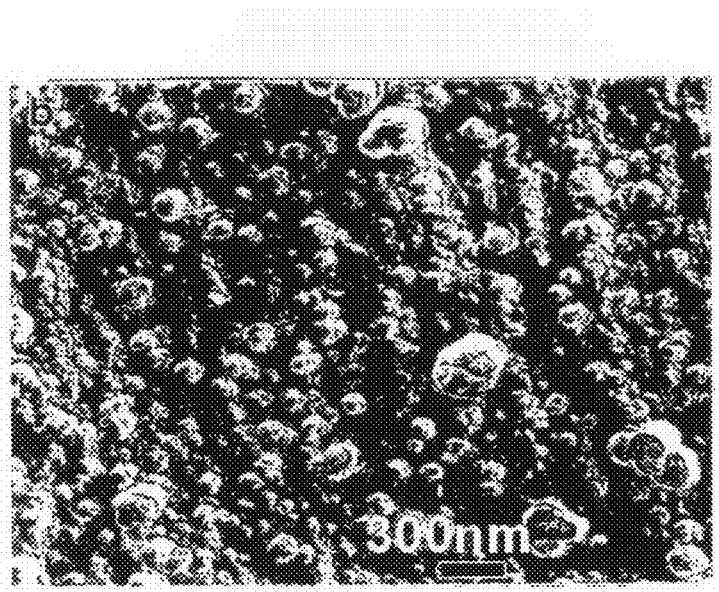
FIG. 2b: Freeze fracture electron micrograph of E5 (5.0 mg mL$^{-1}$) in water.
Figure 2C:
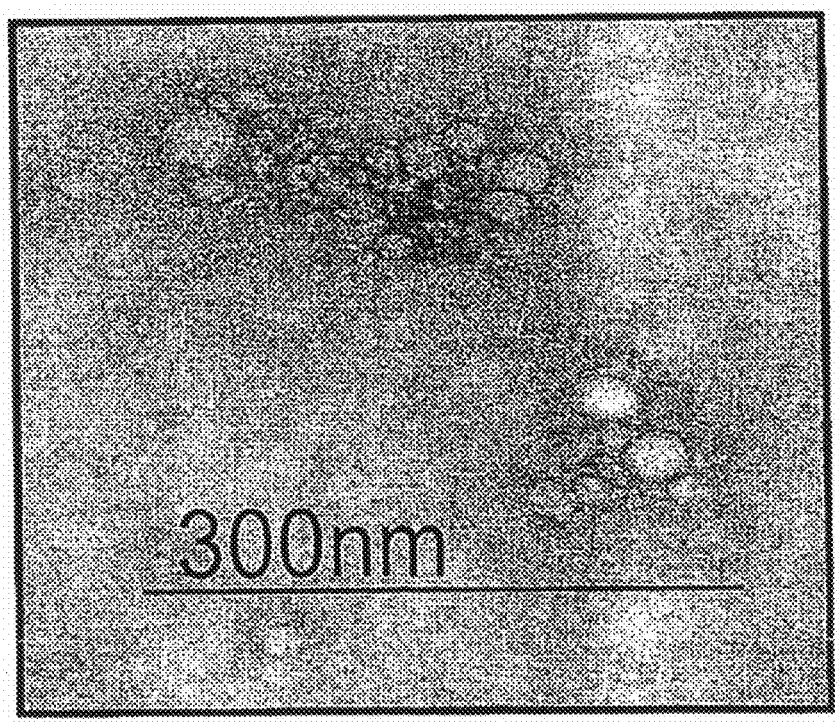
FIG. 2c: Negative stained transmission electron micrograph of C5 (5 mg mL$^{-1}$) in water.

Polymer aggregation was probed with methyl orange [22, 27] (FIG. 2a) and the more hydrophobic polymers (Hydrophobicity Index [HI]=1-2, Hydrophobic Lipophilic Balance [HLB]=17-18) produced more stable aggregates, as evidenced by their low CMCs (<10 μM, FIG. 2a, Table 1). The more hydrophobic polymers also produced more apolar hydrophobic cores as evidenced by the extent of the post micellisation methyl orange hypsochromic shift (λmax<430 nm, Table 1). Polymer aggregates were 100-300 nm in diameter (Table 1), a size inconsistent with the unimolecular aggregation proposed by some authors [28] and both freeze fracture and negative stained transmission electron microscopy revealed a cluster of smaller 10-30 nm aggregates hierarchically organised into larger aggregated (FIGS. 2b and 2c) and, without wishing to be limited by theory, such structures consistent with the model proposed in FIG. 2d. This clustering arrangement is an unusual aggregate for amphiphilic polymers. Block copolymer micelles, for example, are conventional single micelle entities with a diameter of 12-36 nm [29, 30] and micelles prepared from cholesteryl pullulans are also believed to exist as single micelles of 25 nm in diameter [3]).

The molar CMCs of the current polymers when compared to CMC values recorded for other amphiphiles with even lower HLBs reveal that the current aggregates are more stable than other amphiphilic aggregates, such as F127 (Tables 1 & 2). The CMCs of the current polymers differ by 1 to 3 orders of magnitude from those recorded for the Pluronic block copolymer F127 (HLB=14, CMC=550 μM [6]) and polysorbate 20 (HLB=16.7, CMC=53 μM [4]).

Figure 2D:
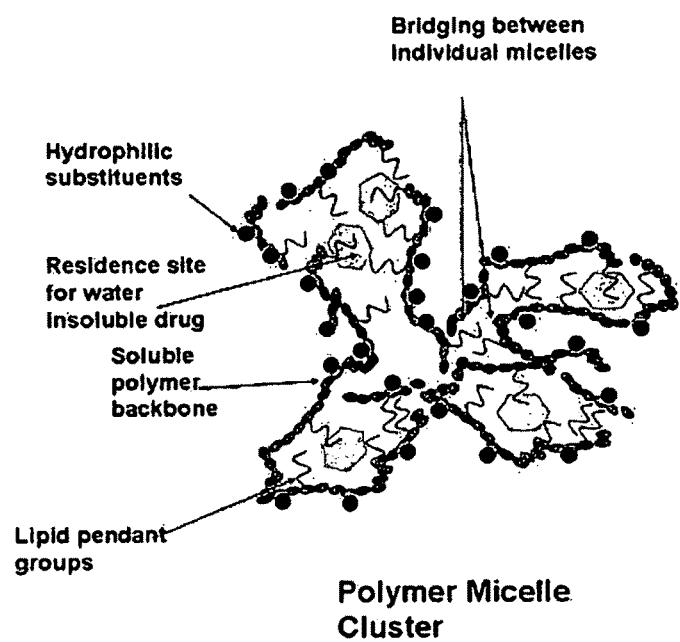
FIG. 2d: Schematic representation of the self assembled polymer micellar cluster.

Without wishing to be limited by theory, the present inventors believe that this more favourable aggregation phenomenon is consistent with the model proposed in FIG. 2d as the ability of the polymer to form multiple inter- and intra-polymer hydrophobic and hydrogen bond associations would contribute to the entropy gain associated with the aggregation event in addition to the loss of water structure accompanying the micellisation event. Additionally an increase in molecular weight favours aggregation (FIG. 2a), once again an observation consistent with the hypothesis that multiple inter and intramolecular contacts stabilise the micellar clusters.

Drug Loading

Figure 3A:
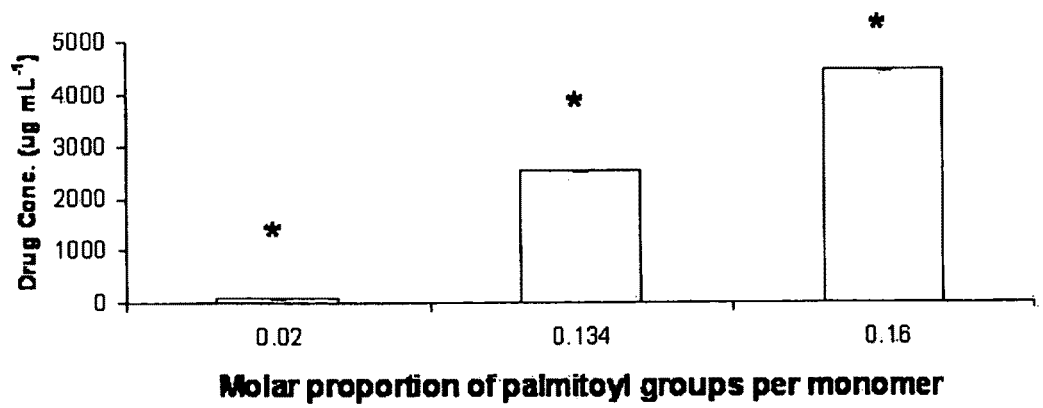
FIG. 3a: Effect of palmitoylation levels on propofol encapsulation. Initial drug concentration=10 mg mL$^{-1}$, initial polymer concentration=5 mg mL$^1$, *=statistically significant difference (p<0.05, n=4), data represent mean±s.d.
Figure 3B:
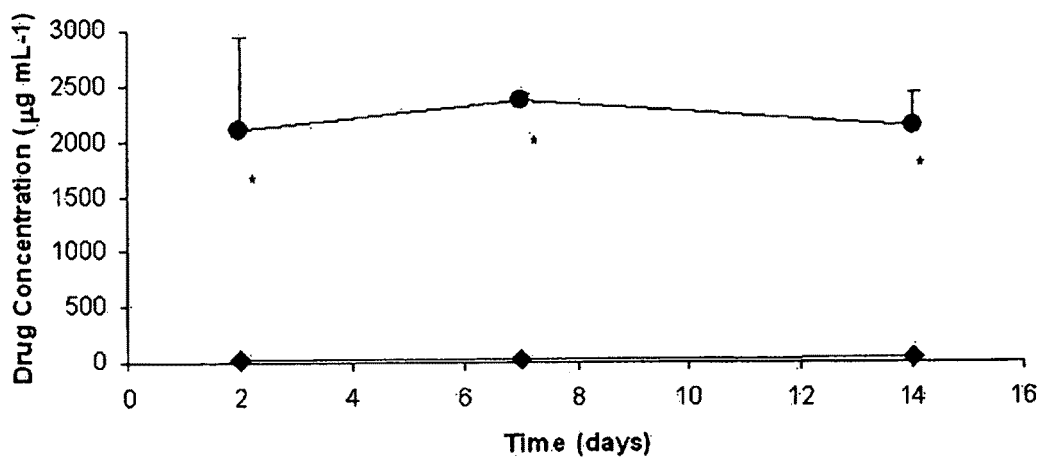
FIG. 3b: The effect of palmitoylation on the encapsulation of propofol (initial polymer concentration=5 mg mL$^{-1}$, initial drug concentration=10 mg mL$^{-1}$); ●=G19+propofol, ◆=GE1+propofol. For HI, approximate HLB and CMC values (where available) see Table 1. *=statistically significantly different (p<0.05). 1 mole of G19 encapsulates 48 moles of propofol. Samples were stored at room temperature.

The formation of more apolar domains, favours hydrophobic drug encapsulation and thus the more hydrophobic polymers encapsulate greater amounts of drug (FIGS. 3a and 3b). Encapsulation levels are high: 5 mg mL$^{-1}$ G42 (Table 1) encapsulates 4.43±0.12 mg mL$^{-1}$ propofol. The micellar clusters transformed to nanoparticle formulations on incorporation of drugs with a high log P such as propofol. Propofol (log P=4.1) resulted in the production of larger particles from the micellar clusters which appeared as dense 50-150 nm particles on electron micrographs (FIG. 5c), while prednisolone (log P=1.4) resulted in isotropic liquids with particle sizes of 10-100 nm in the case of prednisolone—a mixture of drug swollen particles and micellar clusters (inset FIG. 4b).

We have found that an increase in poly(ethylenimine) amphiphile aggregation number is seen in the presence of the hydrophobic molecule—cholesterol [22] and without wishing to be limited by theory, we postulate that the presence of a more hydrophobic drug shifts polymer aggregation from a micellar cluster to a more dense nanoparticle. Propofol levels in the carbohydrate formulations are maintained at above 75% of the initial value for at least 30 days (FIG. 3b). Table 3 shows that if ionisation of the amine groups is suppressed by dialysing the polymer against alkaline media, drug encapsulation levels also increase. Removing the work associated with overcoming electrostatic repulsions, which dominate the early phase of the aggregation step, thus increases drug encapsulation levels.

The increase in drug encapsulation with increase in polymer hydrophobicity has been observed with block copolymers [32, 33]. However, the formation of nanoparticles from block copolymers in the presence of hydrophobic drugs has, to our knowledge, not been reported and hence is a novel feature of the current amphiphiles. For example propofol and F127 (1.78 mg mL$^{-1}$ propofol and 40 mg mL$^{-1}$ F127) form micelles that are 20-40 nm in diameter [33].

Figure 3C:
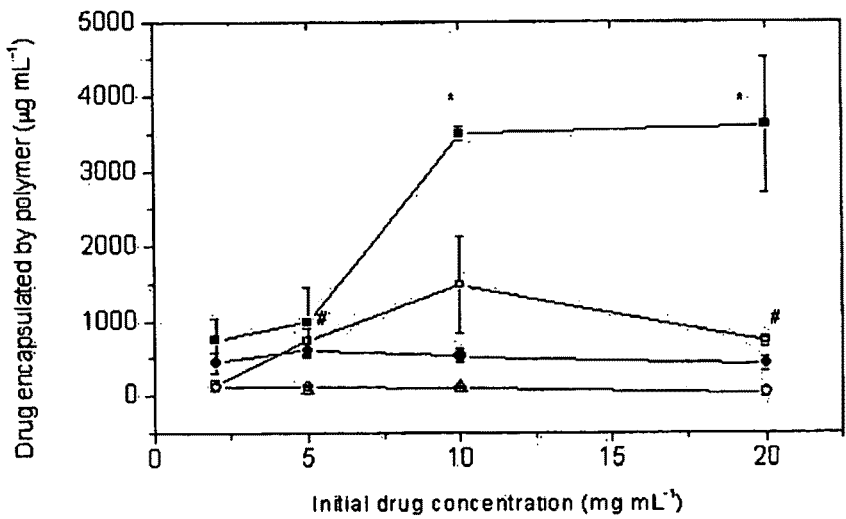
FIG. 3c: The effect of polymer molecular weight on drug encapsulation, drug concentration was measured by HPLC after filtration (0.45 μm); ■=G19 (5 mg mL$^{-1}$), □=G19 (2.5 mg mL$^{-1}$), ●=G4 (5 mg mL$^{-1}$), ○=G4 (2.5 mg mL$^{-1}$), ▲=propofol in water. *=statistically significant difference between polymers at a concentration of 5 mg mL$^{-1}$ and #=statistically significant different between polymers at a concentration of 2.5 mg mL$^{-1}$ (p<0.05).

In addition to polymer HLB/HI (Table 1, FIG. 2a), polymer molecular weight also impacts on micelle stability. An increase in molecular weight increases micelle stability (FIG. 2a) and this improvement in stability is reflected in the influence of molecular weight on drug encapsulation (FIG. 3c). The drug/polymer molar ratio increases 10 fold with a 2.5 fold increase in molecular weight (Table 2). Without wishing to be limited by theory, this observation is once again in agreement with the model proposed in FIG. 2d, as multiple hydrophobic inter and intra molecular contacts are only possible with a lengthy polymer chain.

These carbohydrate drug nanoparticles offer a key advantage over the block copolymers in that molar drug encapsulation levels are at least an order of magnitude higher with the current systems (Table 2 and FIG. 3). Without wishing to be limited by theory, we propose that these higher drug encapsulation levels are due to the nature of the aggregate: namely the formation of a micellar cluster as opposed to single micelles.

It is important to consider not only the efficiency of the amphiphile in incorporating hydrophobic materials into aqueous media but also the maximum level of drug incorporated into aqueous media—a clinically relevant parameter. The latter is also high compared to the block copolymer systems (Table 2). The exceptional drug loading achieved with these carbohydrate amphiphiles approaches 45% w/w, higher than that achieved with other polymeric particles loaded with hydrophobic drugs [19, 34, 35].

Previous studies on hydrophobised carbohydrates have focused on their viscosity enhancing properties [36-38], their ability to form gels [20, 39] and aqueous insoluble aggregates [21, 23, 31, 40-43]. With respect to water soluble carbohydrate amphiphile aggregates [20, 21, 28], characterisation of their ultrastructure and/or bioavailability enhancing effects have not been reported. Here we show that the aggregation behaviour involves a hierarchical organisation of micelles into self repellent colloidal clusters for the first time with direct micrograph evidence supported by dynamic light scattering evidence.

Bioavailability Enhancement with Carbohydrate Drug Carriers

FIGS. 4 and 5 present data on the transport of drugs across biological barriers with these new carbohydrate particles. Drug bioavailability is enhanced quite significantly using these carbohydrate formulations. Two model drugs were chosen: the ocular anti-inflammatory drug prednisolone and the intravenous anaesthetic propofol. On topical application to the eye, aqueous humour levels with 0.35 mg of prednisolone, formulated with the carbohydrate amphiphiles are statistically indistinguishable at early time points from drug levels obtained using 3.5 mg of prednisolone in Prednisolone Forte®. Dilution of Prednisolone Forte was not carried out so as not to destabilise the formulation. No drug was detected with any of the prednisolone formulations in the vitreous humour. These carbohydrate nanoparticles facilitate drug absorption across the cornea to the aqueous humour but fail to deliver drug to the back of the eye. However this is unsurprising in view of the topical mode of delivery and characteristics of the drug [44].

The sleep time obtained with the carbohydrate propofol formulations are up to ten times those obtained when using either the commercial Fresenius or Diprivan® formulations. A loss of righting reflex time could not be recorded with the GCPQ formulations as animals were asleep by the end of the injection administration period (See legend of FIG. 4b); evidence that delivery of the centrally acting drug across the blood brain barrier is rapid and efficient. In order to compare the formulations, the amount of propofol giving rise to each minute of sleep time were compared: values were 0.426 and 0.032 mg min$^{-1}$ with 0.2 mg propofol per mouse (0.1 mL dose volume) of the Fresenius and G19 formulations respectively, 0.134 and 0.023 mg min$^{-1}$ with 0.4 mg propofol per mouse of the Diprivan® and G41 formulations respectively (0.1 mL dose volume), and 152 and 111 mg min$^{-1}$ with 0.5 mg propofol per mouse with the undiluted (10 mg mL$^{-1}$) Fresenius and Diprivan formulations respectively (0.05 mL dose volume). While this strategy may offer anaesthetic induction benefits to propofol as rapid induction is desirable [45], principally these experiments demonstrate that this technology may prove beneficial for the central nervous system delivery of behaviour modification therapies or therapies to treat specific brain diseases.

From the current study, the mechanism by which these carbohydrate amphiphiles improve drug delivery to the CNS or indeed across the cornea is not fully understood, however with respect to the CNS, some indicators may be found in an analysis of the physical properties of the formulations. The particle size and particle size distribution of the commercial propofol formulation, as exemplified with Diprivan® (FIG. 5b), is larger than that seen with the carbohydrate formulation (FIG. 5c). The formulation shown in FIG. 5c was filtered, however unfiltered carbohydrate formulations show no bioavailability efficiency gains when compared to the commercial emulsion formulations (data not shown). Since filtration of polymer aggregates results in a decrease in particle size (Table 1), we hypothesize, without wishing to be held by theory, that the reduced particle size is responsible in part for the drug delivery activity of these carbohydrate nanoparticles.

Furthermore lipid free formulations of propofol have been reported to be accompanied by an increase in potency [46], presumably due to a lack of a lipid reservoir in the blood which would favour partitioning into the brain. It is possible that the lack of a lipid reservoir in the blood with the carbohydrate formulations is also responsible for the increased potency of this formulation observed here.

In conclusion, carbohydrate amphiphiles have been synthesised and found to self-assemble into micellar clusters which provide an enhanced carrying capacity for hydrophobic drug molecules and facilitate the transport of drug molecules across biological barriers, thus enhancing their bioavailability. The current technology offers a solution to pharmaceutical formulators of hydrophobic drugs.

Synthesis of Amphiphilic Carbohydrates with Betaine Groups

Variants of the amphiphilic carbohydrates were synthesised with quaternary betaine groups replacing the quaternary ammonium groups on the a unit. Some of the derivatised carbohydrates described below consisted of a and c units, omitting the b units present in some embodiments of the present invention.

Synthesis and Characterization of Oleyl Betaine Glycol Chitosan and Palmitoyl Betaine Glycol Chitosan Degradation of Glycol Chitosan 1.5 g glycol chitosan (GC) was dissolved in 110 ml 4 M HCl and kept at 50° C. for 48 hours in a shaking water bath. The solution was dialyzed against 5 L water (6 changes) and the dialysate was lyophilised to give a white fibrous solid (523 mg).

Conjugation of Betaine to Glycol Chitosan 0.129 g betaine was dissolved in 10 ml water. To this was added 1.0 g N-Ethyl-N'-(3-dimethylaminopropyl)carbodiimide hydrochloride (EDAC) and the reaction stirred for 15 minutes. Next 0.36 g GC (MW~15-21 kDa) in 40 ml distilled water was added and the reaction stirred for a further 24 hours at 25° C. HCl was added to the solution to the final concentration 0.1 M and the reaction kept stirring for yet another 30 minutes. The reaction solution was dialyzed against 5 L water (6 changes). The dialysate was lyophilised to give a white fibrous solid. The yield was 391 mg.

The Conjugation of Oleyl Groups to Betaine Glycol Chitosan

Betaine Glycol chitosan (GCB, 180 mg) was dissolved in 20 ml water and mixed with sodium bicarbonate solution (150 mg in 20 ml water) to which was added absolute ethanol (30 ml). An ethanolic solution of oleic acid N-hydroxy succinimide (ONS, 5 mg mL$^{-1}$, 30 ml) was added drop wise to this solution and the mixture left stirring for 72 h at room temperature. Ethanol was evaporated under reduced pressure and the solution extracted with diethyl ether (3 times, 60 ml each), dialysed against 5 L water (6 changes), and then lyophilized to give oleyl betaine glycol chitosan (GCBO). The yield was 72 mg.

The Conjugation of Palmitoyl Groups to Betaine Glycol Chitosan

GCB (180 mg) was dissolved in 20 ml water and mixed with sodium bicarbonate solution (150 mg in 20 ml water) to which was added absolute ethanol (30 ml). An ethanolic solution of palmitic acid N-hydroxysuccinimide (PNS, 5.28 mg mL$^{-1}$, 30 ml) was added drop wise to this solution and the mixture left stirring for 72 h at room temperature. Ethanol was evaporated under reduced pressure and the solution extracted with diethyl ether (3 times, 60 ml each), dialysed against 5 L water (6 changes), and then lyophilized to give palmitoyl betaine glycol chitosan (GCBP). The yield was 76 mg.

Characterization of Oleyl Betaine Glycol Chitosan and Palmitoyl Betaine Glycol Chitosan The molecular weight of the degraded glycol chitosan was determined by multi-angle laser light scattering and gel permeation chromatography (GPC/MALLS, MiniDawn, Wyatt, USA), using acetate buffer as mobile phase (23).

$^1$H NMR spectra were recorded using a Bruker AMX 400 MHz spectrometer (Bruker Instruments, UK). D$_2$O was used as the solvent for depolymerised glycol chitosan, whereas CD$_3$OD was used for the derivatised polymers.

UV-Visible Spectrophotometry

A solution of methyl orange (25 µM) was prepared in borate buffer (0.02 M, pH 9.4) and used as a diluent in preparing a high concentration of GCBO and GCBP (15 mg mL$^{-1}$) by probe sonication. These GCBO and GCBP formulations were subsequently diluted with the methyl orange solution and the dilutions were incubated for 1 h at room temperature before their ultra-violet absorption spectra were recorded (300-600 nm) using a UV spectrophotometer (UNICAM UV 300, Thermo Spectronic, UK).

Isothermal Titration Calorimetry

Formulations of GCB (2 mg/ml) and GCBP (1.92 mg/ml) in water were prepared by probe sonication and demicellisation enthalpograms were recorded using a Microcal isothermal titration calorimeter (MICROCAL™ VP-ITC, UK).

Dynamic Light Scattering

Particle size and surface charge measurements were carried out with a Zetasizer 3000 HS (Malvern Instruments, Worcs., UK) at 25° C. Scattered light was detected at a 90° angle. All samples were passed through a membrane filter (pore size: 450 nm, Millipore) prior to filtration.

Degradation of Glycol Chitosan

4M HCl was used to degrade the glycol chitosan for 48 hours. The molecular weight of the degraded GC was 15 k-21 kDa as determined by gel permeation chromatography.

Conjugation of Betaine to Glycol Chitosan

The betaine levels of the polymer were determined using $^1$H NMR and calculating the ratio of quaternised betaine CH$_3$ groups (δ 3.1, 9H) to the sugar groups (H-2 to H-11, δ 3.5-4.5, 10H). It was found that the molar proportion of the monomer units conjugated to betaine was 0.122.

The Conjugation of Oleyl or Palmitoyl Groups to Betaine Glycol Chitosan

The level of oleyl or palmitoyl groups conjugated to betaine glycol chitosan was determined using $^1$H NMR by calculating the ratio of CH$_3$ groups in the palmitoyl or oleyl chains (δ 0.880, 3H) to the sugar groups (H-2 to H-11, δ 3.5-4.5, 10H). The molar proportion of monomer units conjugated to oleyl groups in oleyl betaine glycol chitosan was found to be 0.198 and the molar proportion of monomer units conjugated to palmitoyl groups in palmitoyl betaine glycol chitosan was found to be 0.296.

Critical Micelle Concentration (CMC) of GCBO and GCBP

The critical micelle concentrations (CMCs) of GCBO and GCBP were determined by isothermal titration calorimetry (ITC) and UV/VIS spectrophotometry, the latter using methyl orange as a probe. Using ITC the CMCs of GCBO and GCBP were measured as 0.06 mg mL$^{-1}$ and 0.087 mg mL$^{-1}$ respectively. While, using the methyl orange probe, the CMCs of GCBO and GCBP were measured as 2.4 mg mL$^{-1}$ and 0.78 mg mL$^{-1}$ respectively. The differences in the values stem from the different methods used. All CMC data is shown in Table 5.

TABLE 5

Data of GCBO and GCBP

| Sample | Molar proportion of betaine groups per monomer | Molar proportion of hydrophobic substituents per monomer | CMC (g L$^{-1}$) | Methyl Orange λmax (nm) |
|---|---|---|---|---|
| GCBO | 0.122 | Oleyl = 0.198 | 0.06*/2.4# | 433 |
| GCBP | 0.122 | Palmitoyl = 0.296 | 0.087*/0.78# | 423 |

*= Determination using ITC
= Determination using the hypsochromic shift of methyl orange Size Measurements of GCBO and GCBP Aggregates The sizes and surface charges of GCBO and GCBP aggregates are listed in Table 6. For GCBO samples, two peaks were detected indicating that two types of aggregates are formed for this polymer. For the GCBP samples only one broad peak was detected. Both polymer samples showed larger aggregates in water than in borate buffer, due presumably to charge repulsion of the polymer positive charges at the lower pH and all particles reported a slight positive zeta potential.

TABLE 6

Sizes and surface charge of GCBO and GCBP

| | Particle size (nm), Concentration = 3 g L$^{-1}$ | | Particle surface charge (mv), Concentration = 3 g L$^{-1}$ | |
|---|---|---|---|---|
| Sample | In H$_2$O | In Borax | In H$_2$O | In Borax |
| GCBO | 67.5/300 nm | 92/250 nm | 3.1 | 3.1 |
| GCBP | 360 nm | 180 nm | 3.0 | 3.1 |

An Alternative Method for the Synthesis of Quaternary Ammonium Oleyl Glycol Chitosan and Quaternary Ammonium Palmitoyl Glycol Chitosan Quaternisation of GC 0.75 g of GC which had been degraded in 4M HCL (as detailed above but for 15 h instead of 48 h) was stirred for 2 h in 225 ml of N-methylpyrrolidone containing 2 mg mL$^{-1}$ sodium iodide. 45 mL of ethanolic sodium hydroxide was added (10 mg mL$^{-1}$) and typically 4.6 mL of methyl iodide. The mixture was stirred under nitrogen at 36° C. for 4 h before being precipitated using excess diethyl ether. The precipitate was washed with diethyl ether, washed subsequently with ethanol, redissolved in water and dialyzed against 5 L 0.1M NaCl (3 changes) and 5 L water (6 changes). The dialysate was lyophilised to give GCQ as a white fibrous solid. The yield was 282 mg.

The Conjugation of Oleyl or Palmitoyl Groups to Quaternary Ammonium Glycol Chitosan GCQ (134 mg) was used to prepare oleyl and palmitoyl conjugates of GCQ using an analogous method to that used to prepare oleyl and palmitoyl derivatives of betaine glycol chitosan. The yield of quaternary ammonium oleyl glycol chitosan (GCQO) was 165 mg and the yield of quaternary ammonium palmitoyl glycol chitosan (GCQP) was 87 mg.

Characterization of GCQO and GCQP

Characterization of the GCQO and GCQP was carried out as described above to determine the molecular weight of glycol chitosan and the level of glycol chitosan substitution using gel permeation chromatography with multi-angle laser light scattering and $^1$H NMR spectrometry respectively.

Results

Degradation of Glycol Chitosan

The molecular weight of glycol chitosan was 17-21 kDa.

Quaternisation of Glycol Chitosan

The quaternisation level of the polymer was determined using $^1$H NMR to calculate the ratio of quaternary ammonium methyl protons (CH$_3$, δ 3.31, 3H) to the level of sugar protons (H-2 to H-11, δ 3.5-4.5, 10H). The molar proportion of quaternary ammonium groups per monomer unit was 0.097.

Oleyl and Palmitoyl levels in Quaternary Ammonium Oleyl Glycol Chitosan and Quaternary Ammonium Palmitoyl Glycol Chitosan.

The oleyl levels of the polymer were determined using $^1$H NMR to calculate the ratio of CH=CH groups in the oleyl substituent (δ 5.3, 2H) to the sugar groups (H-2 to H-11, δ 3.5-4.5, 10H). The molar proportion of oleyl groups per monomer in quaternary ammonium oleyl glycol chitosan was found to be 0.319. The palmitoyl level in quaternary ammonium palmitoyl glycol chitosan was determined using $^1$H NMR by calculating the ratio of methyl protons in the palmitoyl chains (δ 0.88, 3H) to the methine/methylene protons in the sugar groups (H-2 to H-11, δ 3.5-4.5, 10H). The molar proportion of palmitoyl groups per monomer in quaternary ammonium palmitoyl glycol chitosan was 0.381.

Biological Evaluation

Topical Ocular Administration of Prednisolone

Male New Zealand White rabbits (n=4, Harlan, UK) were dosed with prednisolone formulations (35 μL) into the lower cul de sac of each eye using an air displacement pipette. At 1 h, 2 h and 4 h after dosing, animals were killed and the aqueous humour sampled with a syringe. The vitreous humour was then collected and all biological samples immediately frozen in liquid nitrogen. Samples of aqueous humour were thawed and analysed by diluting 50 μL of aqueous humour with 15 μL of mobile phase containing the internal standard. These diluted samples were analysed by HPLC as described above. Samples of vitreous humour (0.5 mL) were also thawed and extracted with ethyl acetate [50] prior to analysis.

Intravenous Central Nervous System Delivery of Propofol

Male six week old MF1 mice were injected intravenously via the tail vein with various propofol formulations and both the time to loss of righting reflex and the sleep time were recorded. The loss of righting reflex was confirmed in animals immediately after dosing, by an animal failing to right itself when placed on its back and animals which failed to sleep were recorded as having a sleep time of 0 min.

Oral Absorption Potential of Carbohydrate Amphiphiles

The oral absorption potential of carbohydrate amphiphiles was assessed. Cyclosporine A (CsA)—carbohydrate micellar formulations were prepared as described above using a carbohydrate amphiphile with a nominal molecular weight of 15-30 kDa with a molar proportion of quaternary ammonium groups per monomer of 0.169 and a molar proportion of palmitoyl groups per monomer of 0.155.

Adult male Wistar rats [(Harlan Olac, UK), weight 240-280 g, n=4] were fasted for 12 h before the intragastric administration of CsA (2 mg mL$^{-1}$, 1 mL, 7.5 mg kg$^{-1}$) and for a further 4 h thereafter. CsA was administered either as a dispersion of the drug in water (dispersed by probe sonication), a polymer formulation or the commercial liquid formulation Neoral® (100 mg mL$^{-1}$) which had been diluted with distilled water to give a solution of 2 mg mL$^{-1}$. At various time intervals blood (200 μL) was sampled from the tail vein of anaesthetised rats and CsA blood levels analysed using a monoclonal antibody radioimmunoassay kit (Cyclo-Trac SP-Whole Blood Radioimmunoassay Kit, Diasorin, UK) in accordance with the manufacturers instructions.

Figure 6A:
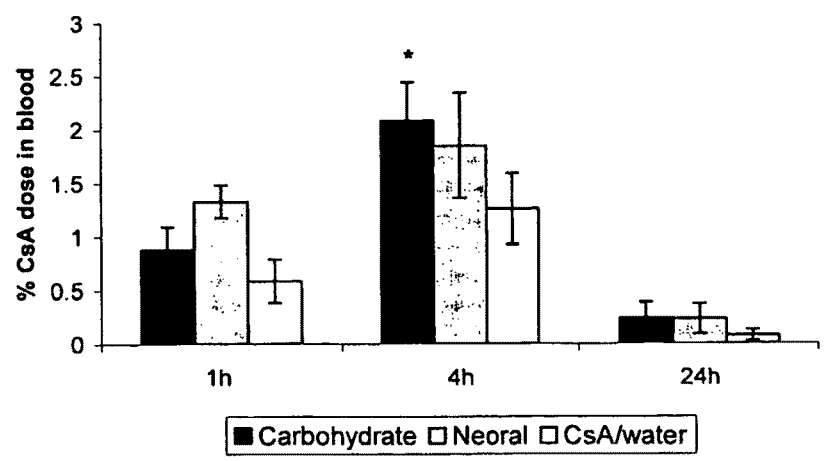
FIG. 6a: Blood levels of cyclosporine A (CsA) following the oral administration of carbohydrate formulations. Animals were dosed with 7.5 mg kg$^{-1}$ CsA and drug, polymer ratio=6.7:1. *=statistically significantly different from CsA in water (p<0.05).
Figure 6B:
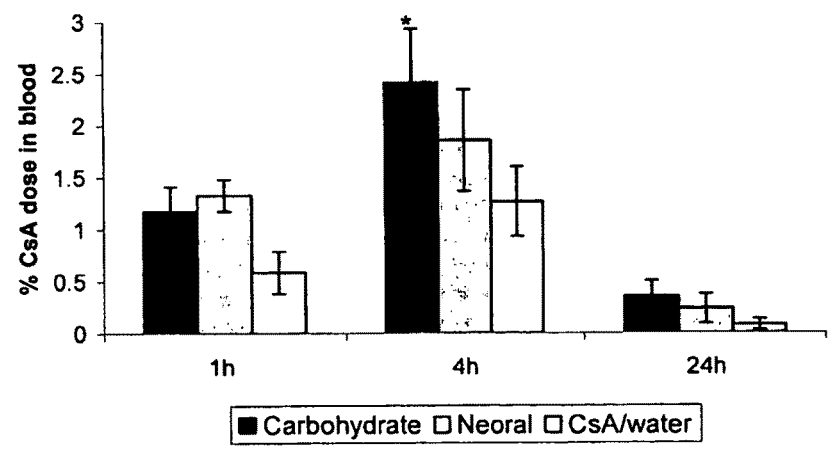
FIG. 6b: Blood levels of CsA following the oral administration of carbohydrate formulations. Animals were dosed with 7.5 mg kg$^{-1}$ CsA and drug, polymer ratio=10:1. *=statistically significantly different from CsA in water (p<0.05)
Figure 6C:
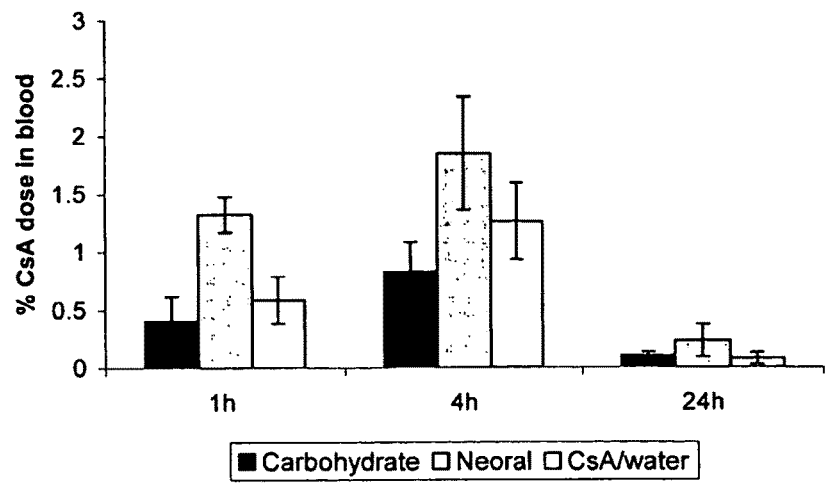
FIG. 6c: Blood levels of CsA following the oral administration of carbohydrate formulations. Animals were dosed with 7.5 mg kg$^{-1}$ CsA and drug, polymer ratio=13.3:1.

These results are shown in FIGS. 6a to 6c and demonstrate that quaternary ammonium palmitoyl glycol chitosan improves the oral absorption of CsA by increasing blood levels by between 100 and 350%.

Stability of GCPQ Formulations and Dissolution Testing

GCPQ was synthesized as described herein and the polymer characteristics are depicted in Table 4.

TABLE 7

Characterisation of GCPQ

| Polymer | MW Glycol chitosan starting material (kDa) | CMC (g L$^{-1}$) | Polymer - drug particle mean size (nm) | Mole % Palmitoyl groups | Mole % Quaternary Ammonium groups |
|---|---|---|---|---|---|
| GCPQ | 17 | 2.27 | 254 | 15.52 | 16.91 |

Formulations were then prepared by dispersing of GCPQ (20 mgmL$^{-1}$) and Cyclosporine A (CsA, 5 mg mL$^{-1}$) using probe sonication (probe sonication on ice for 10 minutes with the instrument set at 75% of its maximum output). Both liquid and freeze-dried formulations were stored at 8–10° C. for 6 months. At one month time intervals, reconstituted freeze-dried samples (reconstituted in distilled water) and liquid samples were filtered (0.45 μm) and analysed by HPLC.

HPLC Analysis

High performance liquid chromatography analysis was carried out using a Waters 515 HPLC Pump, Waters 717 plus Autosampler and Waters 468 Tunable Absorbance Detector.

Figure 7:
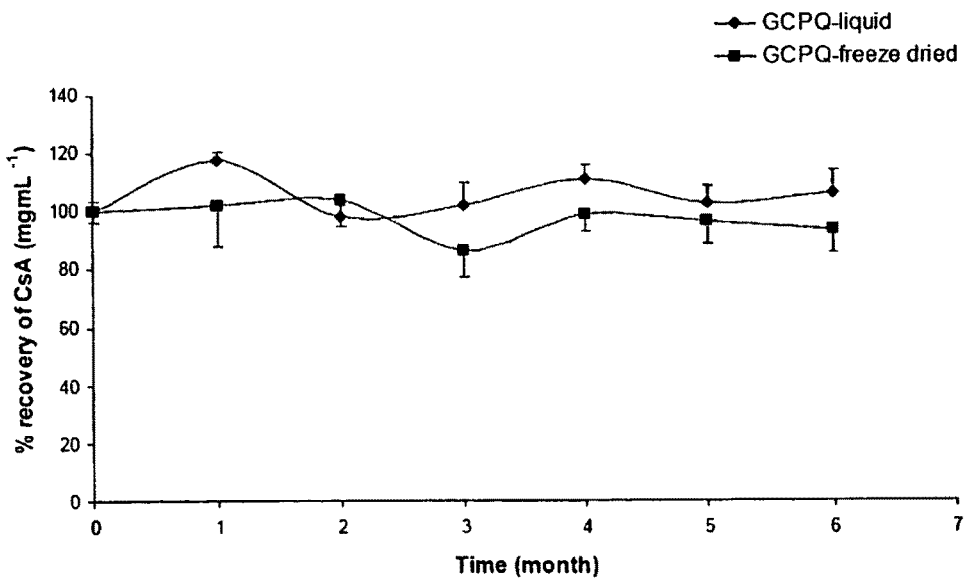
FIG. 7: Percentage recovery of CsA from GCPQ-CsA formulations. The means are not statistically significantly different (p>0.05).

Samples were chromatographed on a reversed phase column (Waters Asymmetry Spherisorb ODS2, 5 μm particle size, 250×4.6 mm) which was maintained at 80° C. with a Jones Chromatography Column Heater model 7971. The mobile phase was acetonitrile, water, tert-butyl-methyl-ether, phosphoric acid (600:350:50:1) at a flow rate of 1.2 mL min$^{-1}$. CsA peak detection was at 210 nm. Data was analyzed using Waters Empower software. Results are shown in FIG. 7.

Tablet Preparation

Various GCPQ-CsA tablets were prepared by direct compression. All powders were sieved (35-mesh) and compressed into 5 mm diameter tablets (EKO model single-punch tablet machine, Erweka, Germany). The compression force was adjusted separately for each formulation so that the corresponding crushing strengths of tablets were at a maximum level.

Dissolution Testing

Figure 8:
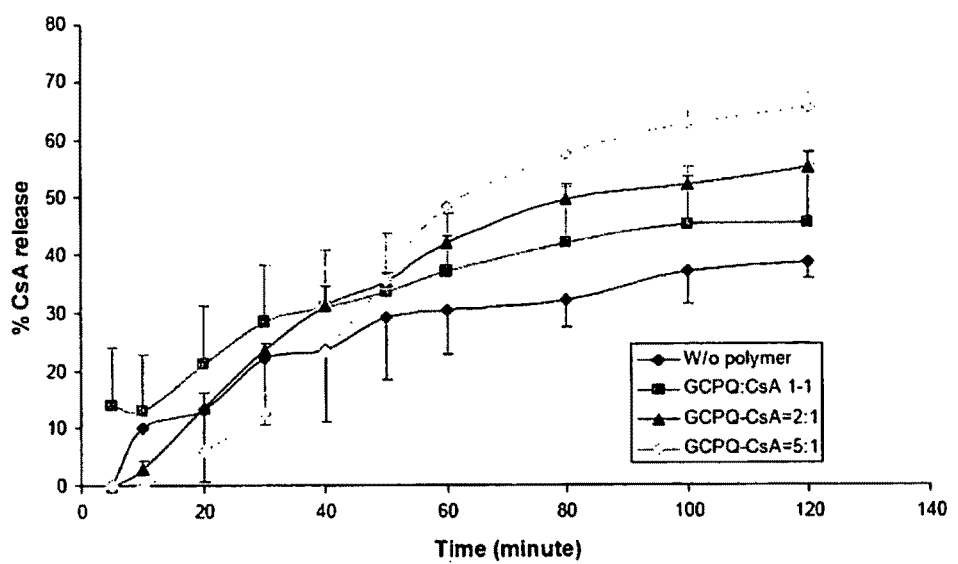
FIG. 8: CsA release profiles from various GCPQ-CsA tablets (n=3, mean±SD)

Dissolution testing was performed on three tablets from each of the above formulations using a modified USP24-NF19 method: USP apparatus 2 (Erweka DT6R Dissolution Tester) at a stirring speed of 30 rpm, with 1000 mL distilled water as the dissolution medium. Samples were taken after 5, 10, 20, 40, 60, 80 and 120 minutes filtered (0.45 μm) and subsequently analysed by HPLC as described above. Results are given in FIG. 8 below.

TABLE 8

CSA Tablet formulations

| Composition for 1 tablet | Formula 1 (mg) Without polymer | Formula 2 (mg) CsA, GCPQ = 1:1 | Formula 3 (mg) CsA, GCPQ = 1:2 | Formula 4 (mg) CsA, GCPQ = 1:5 |
|---|---|---|---|---|
| CsA | 5 | 5 | 5 | 5 |
| Mannitol | 100 | 100 | 100 | 100 |
| Avicel | 100 | 100 | 100 | 100 |
| Stearic acid | 5 | 5 | 5 | 5 |
| SDS | 2 | 2 | 2 | 2 |
| GCPQ | — | 5 | 10 | 25 |

TABLE 1

| Sample | Mw glycol chitosan starting material (KDa) | Initial gravimetric feed ratio of PNS:GC | Molar proportion of palmitoyl groups per monomer (L) | Initial gravimetric feed ratio of methyl iodide:GC | Molar proportion of quaternary ammonium groups per monomer (Q) | HI | HLB | CMC (g L$^{-1}$/ μM) | Carbohydrate aggregate mean particle size/ polydispersity | Mean particle size after filtration/ polydispersity | Mean Particle size polydispersity after drug loading and filtration | Final Methyl orange λmax (nm) |
|---|---|---|---|---|---|---|---|---|---|---|---|---|
| A1 | 15 | 0.26 | 0.0215 | 5.02 | 0.1074 | 5 | 19.7 | 1.76/106 | 259/0.16 | 184/0.09 | 163/0.07 | 442 |
| A5 | 15 | 2.11 | 0.1508 | 5.02 | 0.1649 | 1.09 | 17.9 | 0.17/8.93 | 241/0.14 | 201/0.12 | n.d. | 426 |
| C3 | 15 | 1.06 | 0.1028 | 9.58 | 0.2015 | 2.22 | 18.5 | 0.09/4.9 | 200/0.27 | 178/0.22 | n.d. | 428 |
| E1 | 15 | 0.26 | 0.0196 | 14.14 | 0.1189 | 5.69 | 19.7 | 0.80/47.9 | 303/0.37 | 172/0.06 | 170/0.13 | 438 |
| E5 | 15 | 2.11 | 0.117 | 14.14 | 0.13 | 1.11 | 18.3 | 0.11/5.9 | 230/0.39 | 163/0.33 | 209/0.10 | 426 |
| C5 | 19 | 2.11 | 0.123 | 9.58 | 0.221 | 1.8 | — | — | — | — | — | — |
| G2 | 15 | 0.79 | 0.168 | 18.24 | 0.743 | 4.4 | 17.8 | 0.08/4.0 | 348 | 147 | 154 | 432 |
| G3 | 15 | 1.58 | 0.134 | 9.13 | 0.337 | 2.3 | 18 | 0.11/6.1 | 315 | 152 | — | 429 |
| G19 | 10 | 2.11 | 0.134 | 14.14 | 0.134 | 1 | 18 | — | — | — | — | — |
| G42 | 10 | 2.11 | 0.16 | 14.14 | 0.137 | 1.17 | 17.6 | — | — | — | — | — |
| G41 | 10 | 2.11 | 0.185 | 14.14 | — | — | — | — | — | — | — | — |
| GE1 | 10 | 0.26 | 0.02 | 14.14 | 0.119 | 5.95 | 19.7 | — | — | — | — | — |
| G4 | 4 | 2.11 | 0.151 | 14.14 | 0.1263 | 0.84 | 17.7 | 0.363/76.8 | — | 132/0.63 | — | 432 |

TABLE 2

| Drug | Log P | Amphiphile | Mw (kDa) | HLB | CMC (μM) | Moles drug encapsulated per mole of polymer | Drug Concentration (g L$^{-1}$) |
|---|---|---|---|---|---|---|---|
| Propofol | 4.1 | G19 | 11.7 | 18 | — | 48 | 3.6 |
| | | G4 | 4.7 | 17.7 | 76.8 | 3.2 | 0.61 |
| | | F127 | 12.6 | 14 | 550 [6] | 3 [33] | 1.78 |
| | | 2-hydroxypropyl-β-cyclodextrin | 1.3 | — | — | 0.75 [10] | 38.7 |
| Prednisolone | 1.4 | G2 | 19.9 | 17.8 | 4 | 67 | 1.2 |
| | | F127 | 12.6 | 14 | 550 | 0.21 | 0.5 |

TABLE 3

| Disperse Phase | Drug concentration (mg mL$^{-1}$) encapsulated in G19 (5 mg mL$^{-1}$) dialysed against sodium chloride solution (0.1M) and water. Initial drug concentration = 10 mg mL$^{-1}$, mean ± s.d. (n = 4) | Drug concentration encapsulated in G19 (5 mg mL$^{-1}$) dialysed against alkaline sodium chloride solution (sodium chloride - 0.1M, sodium bicarbonate - 0.01M). Initial drug concentration = 10 mg mL$^{-1}$, mean ± s.d. (n = 4) |
|---|---|---|
| Water | 1.52 ± 0.47 | 3.45 ± 0.02* |
| Phosphate Buffered Saline (pH = 7.4) | 1.32 ± 0.07 | 2.16 ± 0.04* |
| Glucose (5% w/v) | 0.35 ± 0.05 | 1.75 ± 0.04* |

*= statistically significant difference between alkaline and neutral dispersions (p < 0.05)

REFERENCES

The references cited herein are all expressly incorporated by reference in their entirety 1. Kilpatrick P. Pressures in the pipeline. *Nature Drug Discovery* 2, 337 (2003)
2. Wenlock M. C., Austin R. P., Barton P., Davis A. M. & Leeson P. D. A comparison of physicochemical property profiles of development and marketed oral drugs. *J. Med. Chem.* 46, 1250-1256 (2003)
3. Rowe R. C., Sheskey P. J. & Weller P. J., *Handbook of Pharmaceutical Excipients*. 2003, London: Pharmaceutical Press.
4. Florence A. T. & Attwood D., *Physicochemical Principles of Pharmacy*. 1998, Basingstoke: Macmillan Press.
5. Cheng H. Y. & Holl W. W. Micellar aggregation of Poloxamer 213 and its interaction with cholesterol derivatives. *J. Pharm. Sci.* 79, 907-912 (1990)
6. Alexandridis P., Holzwarth J. F. & Hatton T. A. Micellization of Poly(Ethylene Oxide)-Poly(Propylene Oxide)-Poly(Ethylene Oxide) Triblock Copolymers in Aqueous-Solutions—Thermodynamics of Copolymer Association. *Macromolecules* 27, 2414-2425 (1994)
7. Nam Y. S. et al. New micelle-like polymer aggregates made from PEI-PLGA diblock copolymers: micellar characteristics and cellular uptake. *Biomaterials* 24, 2053-2059 (2003)
8. Krishna A. K. & Flanagan D. R. Micellar solubilisation of a new antimalarial drug, b-arteether. *J. Pharm. Sci.* 78, 574-576 (1989)
9. Strickley R. G. Solubilizing excipients in oral and injectable formulations. *Pharm. Res.* 21, 201-230 (2004)
10. Trapani G., Lopedota A., Franco M., Latrofa A. & Liso G. Effect of 2-hydroxypropyl-b-cyclodextrin on the aqueous solubility of the anaesthetic agent, propofol (2,6-diisopropylphenol). *Int. J. Pharm.* 139, 215-218 (1996)
11. Arnanson T. & Elworthy P. H. Effects of structural variables of non-ionic surfactants on micellar properties of solubilisation: surfactants based on erucyl and behenyl (C22) alcohols. *J. Pharm. Pharmacol.* 32, 381-385 (1980)
12. Ong J. T. H. & Manoukian E. Micellar solubilisation of timobesone acetate in aqueous and aqueous propylene glycol solutions of non-ionic surfactants. *Pharm. Res.* 5, 704-708 (1988)
13. Shuai X., Ai H., Nasongkla N., Kim S. & Gao J. Micellar carriers based on block copolymers of poly($\epsilon$-caprolactone) and poly(ethylene glycol) for doxorubicin delivery. *J. Control. Rel.* 98, 415-426 (2004)
14. Kwon G. S. & Kataoka K. Block copolymer micelles as long-circulation drug vesicles. *Adv. Drug Del. Rev.* 16, 295-309 (1995)
15. Allen C., Maysinger D. & Eisenberg A. Nano-engineering block copolymer aggregates for drug delivery. *Coll. Surfaces. B: Biointerfaces.* 16, 3-27 (1999)
16. Jones M. C. & Leroux J. C. Polymeric micelles—a new generation of colloidal drug carriers. *Eur. J. Pharm. Biopharm.* 48, 101-111 (1999)
17. Torchilin V. P. Structure and design of polymeric surfactant-based drug delivery systems. *J. Control. Rel.* 73, 137-172 (2001)
18. Savic R., Luo L., Eisenberg A. & Maysinger D. Micellar nanocontainers distribute to defined cytoplasmic organelles. *Science* 300, 615-618 (2003)
19. Francis M. F., Lavoie L., Winnik F. M. & Leroux J. C. Solubilization of cyclosporin A in dextran-g-polyethyleneglycolalkyl ether polymeric micelles. *Eur. J. Pharm. Biopharm.* 56, 337-346 (2003)
20. Uchegbu I. F. et al. Quarternary ammonium palmitoyl glycol chitosan—a new polysoap for drug delivery. *Int. J. Pharm.* 224, 185-199 (2001)
21. Miwa A. et al. Development of novel chitosan derivatives as micellar carriers of taxol. *Pharm. Res.* 15, 1844-1850 (1998)
22. Wang W., Qu X., Gray A. I., Tetley L. & Uchegbu I. F. Self assembly of cetyl linear polyethylenimine to give micelles, vesicles and nanoparticles is controlled by the hydrophobicity of the polymer. *Macromolecules* 37, 9114-9122 (2004)
23. Wang W., Mcconaghy A. M., Tetley L. & Uchegbu I. F. Controls on polymer molecular weight may be used to control the size of palmitoyl glycol chitosan polymeric vesicles. *Langmuir* 17, 631-636 (2001)
24. Discher D. E. & Eisenberg A. Polymer vesicles. *Science* 297, 967-973 (2002)
25. Wang W., Tetley L. & Uchegbu I. F. A new class of amphiphilic poly-L-lysine based polymers forms nanoparticles on probe sonication in aqueous media. *Langmuir* 16, 7859-7866 (2000)
26. Gref R. et al. Biodegradable long circulating polymeric nanospheres. *Science* 263, 1600-1603 (1994)
27. Wang G. J. &. Engberts J. Synthesis and Catalytic Properties of Cross-Linked Hydrophobically Associating Poly(Alkylmethyldiallylammonium Bromides). *J. Org. Chem.* 59, 4076-4081 (1994)
28. Yoshioka H., Nonaka K., Fukuda K. & Kazama S. Chitosan-Derived Polymer-Surfactants and Their Micellar Properties. *Biosci. Biotechnol. Biochem.* 59, 1901-1904 (1995)
29. Kabanov A. V. et al. A New Class of Drug Carriers—Micelles of Poly(Oxyethylene)-Poly(Oxypropylene) Block Copolymers as Microcontainers for Drug Targeting from Blood in Brain. *J. Control. Rel.* 22, 141-158 (1992)

30. Yu B. G., Okano T., Kataoka K. & Kwon G. Polymeric micelles for drug delivery: solubilization and haemolytic activity of amphotericin B. *J. Control. Rel.* 53, 131-6. (1998)
31. Akiyoshi K., Deguchi S., Moriguchi N., Yamaguchi S. & Sunamoto J. Self-aggregates of hydrophobized polysaccharides in water, formation and characteristics of nanoparticles. *Macromolecules* 26, 3062-3068 (1993)
32. Rekatas C. J. et al. The effect of hydrophobe chemical structure and chain length on the solubilisation of griseofulvin in aqueous micellar solutions of block copoly(oxyalkylene)s. *Phys. Chem. Chem. Phys.* 3, 4769-4773 (2001)
33. Dwyer C., Viebke C. & Meadows J. Propofol induced micelle formation in aqueous block copolymer solutions. *Coll. Surfaces A: Eng. Aspects* 254, 23-30 (2005)
34. Kim S. Y. & Lee M. Y. Taxol-loaded block copolymer nanospheres composed of methoxy poly(ethylene glycol) and poly(e-caprolactone) as novel anticancer drug carriers. *Biomaterials* 22, 1697-1704 (2001)
35. Francis M. F., Piredda M. & Winnik F. M. Solubilization of poorly water soluble drugs in micelles of hydrophobically modified hydroxypropylcellulose copolymers. *J. Control. Rel.* 93, 59-68 (2003)
36. Landoll L. M. Nonionic polymer surfactants. *J. Polymer Sci. Polymer Chem. Ed.* 20, 443-455 (1982)
37. Kjoniksen A. L. et al. Viscosity of dilute aqueous solutions of hydrophobically modified chitosan and its unmodified analogue at different concentrations of salt and surfactant concentrations. *Langmuir* 13, 4948-4952 (1997)
38. Philppova O. E. et al. Two types of hydrophobic aggregates in aqueous solutions of chitosan and its hydrophobic derivative. *Biomacromolecules* 2, 483-490 (2001)
39. Noble L., Gray A. I., Sadiq L. & Uchegbu I. F. A non-covalently cross-linked chitosan based hydrogel. *Int. J. Pharm.* 192, 173-182 (1999)
40. Wakita M. & Hashimoto M. Bilayer Vesicle Formation of N-Octadecylchitosan. *Kobun. Ronbun.* 52, 589-593 (1995)
41. Uchegbu I. F. et al. Polymeric chitosan-based vesicles for drug delivery. *J. Pharm. Pharmacol.* 50, 453-8 (1998)
42. Lee K. Y., Jo W. H., Kwon I. C., Kim Y. H. & Jeong S. Y. Physicochemical characteristics of self-aggregates of hydrophobically modified chitosans. *Langmuir* 14, 2329-2332 (1998)
43. Kwon S. et al. Physicochemical characteristics of self-assembled nanoparticles based on glycol chitosan bearing 5 beta-cholanic acid. *Langmuir* 19, 10188-10193 (2003)
44. Hughes P. M., Olejnik O., Chang-Lin J. E. & Wilson C. G. Topical and systemic drug delivery to the posterior segments. *Adv. Drug Del. Rev.* 57, 2010-2032 (2005)
45. Langley M. S. & Heel R. C. Propofol: A review of its pharmacodynamic and pharmacokinetic properties and use as an intravenous anaesthetic. *Drugs* 35, 334-372 (1988)
46. Dutta S. & Ebling W. F. Formulation-dependent pharmacokinetics and pharmacodynamics of propofol in rats. *J. Pharm. Pharmacol.* 50, 37-42 (1998)
47. Furusaki E., Ueon Y., Sakairi N., Nishi N. & Tokura S. Facile preparation and inclusion ability of a chitosan derivative bearing carboxymethyl-B-cyclodextrin. *Carbohydr. Polymer* 29, 29-34 (1996)
48. Griffin W. C. *J. Soc. Cosmetic Chem.* 1, 311 (1949)
49. Kan P. L. et al. Highly hydrophilic fused aggregates (microsponges) from a C12 spermine bolaamphiphile. *J. Phys. Chem. B.* 108, 8129-8135 (2004)
50. Rocci M. L. & Jusko W. J. Analysis of prednisone, prednisolone and their 20b-hydroxylated metabolites by high performance liquid chromatography. *J. Chromatogr.* 224, 221-227 (1981)

The invention claimed is:

1. A polymeric micellar aggregate having a mean particle size between 20 nm and 500 nm formed from an amphiphilic carbohydrate polymer, wherein the carbohydrate polymer is:

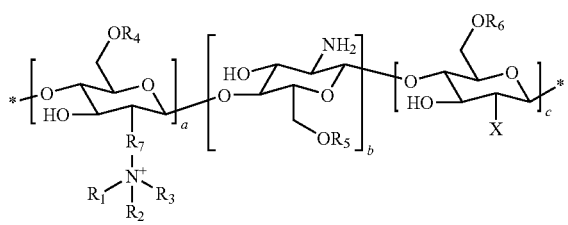

wherein the molar proportion of monomers in the amphiphilic carbohydrate polymer is a+b+c =1.000 and the molar proportion of a is between 0.010 and 0.890, the molar proportion of b is from 0.000 to 0.880, and the molar proportion of c is between 0.110 and 0.990;

and wherein:

X is a hydrophobic group;

$R_1$, $R_2$ and $R_3$ are independently selected from hydrogen or a substituted or unsubstituted alkyl group;

$R_4$, $R_5$ and $R_6$ are independently selected from hydrogen, a substituted or unsubstituted alkyl group, a substituted or unsubstituted ether group, or a substituted or unsubstituted alkene group;

$R_7$ may be present or absent and, when present, is an unsubstituted or substituted alkyl group, an unsubstituted or substituted amine group or an amide group;

or a salt thereof.

2. The polymeric micellar aggregate of claim 1, wherein the molar proportion of the c unit of the carbohydrate polymer is greater than 0.110 and less than 0.400.

3. The polymeric micellar aggregate of claim 1, wherein the molar proportion of the a unit of the carbohydrate polymer is between 0.050 and 0.800.

4. The polymeric micellar aggregate of claim 1, wherein the molar proportion of the b unit of the carbohydrate polymer is between 0.200 and 0.850.

5. The polymeric micellar aggregate of claim 1, wherein the b unit of the carbohydrate polymer is absent from the formula.

6. The polymeric micellar aggregate of claim 1, wherein the hydrophobic group X is selected from a substituted or unsubstituted group which is an alkyl group, an alkenyl group, an alkynyl group, an aryl group, a polyoxa $C_1$-$C_4$ alkylene group or a hydrophobic polymeric substituent.

7. The polymeric micellar aggregate of claim 6, wherein the hydrophobic polymeric substituent is a poly(lactic acid) group, a poly(lactide-co-glycolide) group or a poly(glycolic acid) group.

8. The polymeric micellar aggregate of claim 6, wherein the hydrophobic group X is directly linked to the c unit of the carbohydrate polymer.

9. The polymeric micellar aggregate of claim 6, wherein the hydrophobic group X is linked to the c unit of the carbohydrate polymer via an amine group, an acyl group or an amide group.

10. The polymeric micellar aggregate of claim 1, wherein the hydrophobic group X is $CH_3(CH_2)_n$—CO—, or $CH_3(CH_2)n$-, or $CH_3(CH_2)_p$—CH=CH—$(CH_2)_q$—CO—NH—, or $CH_3(CH_2)_n$CONH—, wherein n is between 4 and 30, and p and q may be the same or different and are between 3 and 15.

11. The polymeric micellar aggregate of claim 1, wherein the hydrophobic group X is produced by coupling a carboxylic acid to an amine group of chitosan.

12. The polymeric micellar aggregate of claim 11, wherein the carboxylic acid is fatty acid.

13. The polymeric micellar aggregate of claim 11, wherein the hydrophobic group X is provided by coupling lauric acid, myristic acid, palmitic acid, stearic acid or arachidic acid to the carbohydrate polymer.

14. The polymeric micellar aggregate of claim 1, wherein the $R_4$, $R_5$ and $R_6$ groups are substituted with one more hydroxy groups or another non-ionic hydrophilic substituent.

15. The polymeric micellar aggregate of claim 1, wherein the $R_4$, $R_5$ and $R_6$ groups are —$(CH_2)_p$—OH, where p is between 1 and 10, or —$(CH_2)_p$—$CH_q(CH_2$—OH$)_r$, where p is between 1 and 10, and q is 0 or 1, and r is 2 or 3, and the sum of q+r=3.

16. The polymeric micellar aggregate of claim 1, wherein the $R_7$ group is absent.

17. The polymeric micellar aggregate of claim 1, wherein $R_7$ is present and is selected from an alkyl group of the formula —$(CH_2)_n$-, an amine group represented by the formula —NH—$(CH_2)_n$- or an amide group represented by the formula —NH—CO—$(CH_2)_n$-, wherein n is 1 to 10.

18. The polymeric micellar aggregate of claim 1, wherein the $R_7$ group is part of a betaine group (—NH—CO—$CH_2$—$N^+R_1R_2R_3$) and $R_7$ is —NH—CO—$CH_2$—.

19. The polymeric micellar aggregate of claim 1, wherein polymeric micellar aggregates have a minimum mean particle size of at least 100 nm and a maximum mean particle size of 400 nm or less.

20. The polymeric micellar aggregate of claim 1, wherein the carbohydrate polymer has a molecular weight between about 1.5 kDa and about 250 kDa.

21. The polymeric micellar aggregate of claim 1, wherein the aggregate is a salt.

22. The polymeric micellar aggregate of claim 21, wherein the salt is formed with a negatively charged ion selected from chloride, iodide, acetate or glutamate ions.

23. A composition comprising a polymeric micellar aggregate as claimed in claim 1.

24. The composition of claim 23, wherein the polymeric micellar aggregate is formulated with a drug.

25. The composition of claim 24, wherein the drug is a hydrophobic drug.

26. The composition of claim 25, wherein the hydrophobic drug is prednisolone, propofol, cyclosporine, oestradiol, testosterone, paclitaxel, etoposide, or amphotericin B.

27. The composition of claim 24, wherein the polymeric micellar aggregate forms nanoparticles with the drug, wherein the nanoparticles have mean diameters between about 20 nm and about 2 μm.

28. The composition of claim 24, wherein the molar ratio of the polymer to the drug in the composition is at least 1:10.

29. A method of making a nanoparticle formulation of a polymeric micellar aggregate and a drug, the method comprising mixing and homogenizing the drug and a polymeric micellar aggregate as claimed in claim 1.

* * * * *

UNITED STATES PATENT AND TRADEMARK OFFICE
CERTIFICATE OF CORRECTION

PATENT NO.       : 8,470,371 B2
APPLICATION NO.  : 12/376827
DATED            : June 25, 2013
INVENTOR(S)      : Uchegbu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1104 days.

Signed and Sealed this
Eighth Day of September, 2015

Michelle K. Lee
*Director of the United States Patent and Trademark Office*